(12) United States Patent
Shibata et al.

(10) Patent No.: US 7,372,561 B2
(45) Date of Patent: May 13, 2008

(54) METHOD AND APPARATUS FOR INSPECTING DEFECTS AND A SYSTEM FOR INSPECTING DEFECTS

(75) Inventors: Yukihiro Shibata, Fujisawa (JP);
Shunji Maeda, Yokohama (JP);
Takafumi Okabe, Yokohama (JP);
Yoichi Takahara, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 366 days.

(21) Appl. No.: 11/139,594

(22) Filed: May 31, 2005

(65) Prior Publication Data

US 2005/0264802 A1    Dec. 1, 2005

(30) Foreign Application Priority Data

May 31, 2004    (JP)    ............................ 2004-160630

(51) Int. Cl.
*G01N 21/00*    (2006.01)
(52) U.S. Cl. .................................................. 356/237.5
(58) Field of Classification Search ...................... None
See application file for complete search history.

(56) References Cited

U.S. PATENT DOCUMENTS 6,571,657 B1 *   6/2003   Olgado et al. ............ 74/490.02
6,935,930 B2 *   8/2005   Fujita ........................... 451/41
7,130,037 B1 *  10/2006   Lange ....................... 356/237.2
2005/0052642 A1  3/2005   Shibata et al.

FOREIGN PATENT DOCUMENTS

JP    2000-155099    6/2000
WO    WO 99/49504    9/1999

* cited by examiner

*Primary Examiner*—Gregory J. Toatley, Jr.
*Assistant Examiner*—Juan D Valentin, II
(74) *Attorney, Agent, or Firm*—Antonelli, Terry, Stout & Kraus, LLP.

(57) ABSTRACT

The present invention relates to a high-sensitivity defect inspection method, apparatus, and system adapted for the fine-structuring of patterns; wherein, in addition to a cleaning tank which chemically cleans a sample and rinses the sample, a defect inspection apparatus having a liquid-immersion element by which the interspace between the sample and the objective lens of an optical system is filled with a liquid, and a drying tank which dries the sample, the invention uses liquid-immersion transfer means from said cleaning tank through said liquid-immersion means of said defect inspection apparatus to said drying tank so that the sample is transferred in a liquid-immersed state from said cleaning tank to said liquid-immersion means.

15 Claims, 15 Drawing Sheets

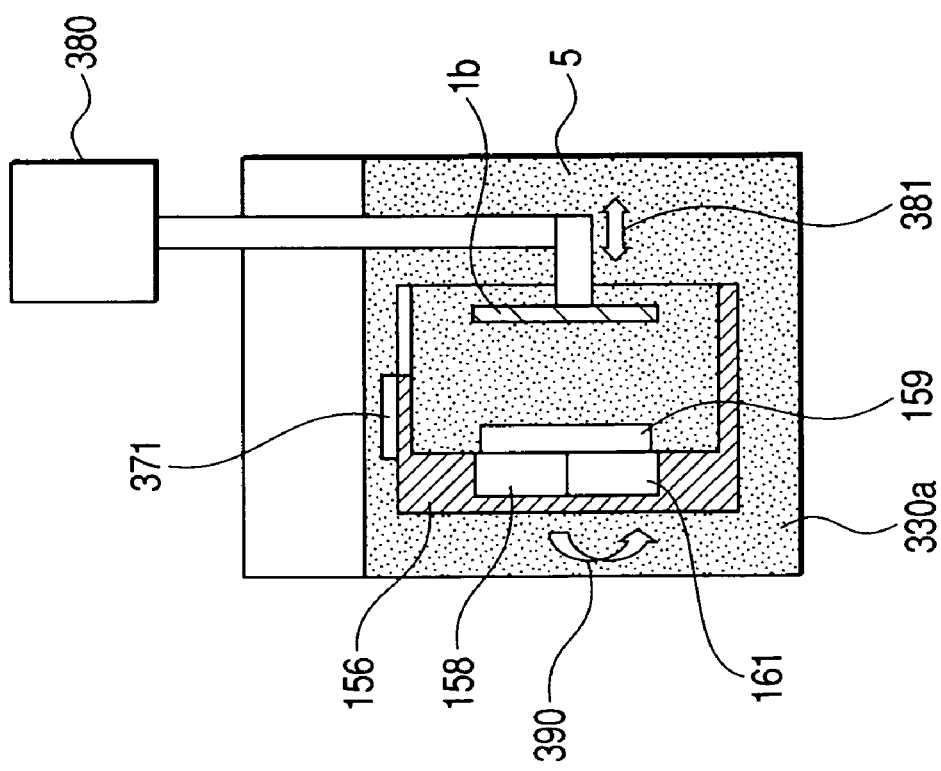
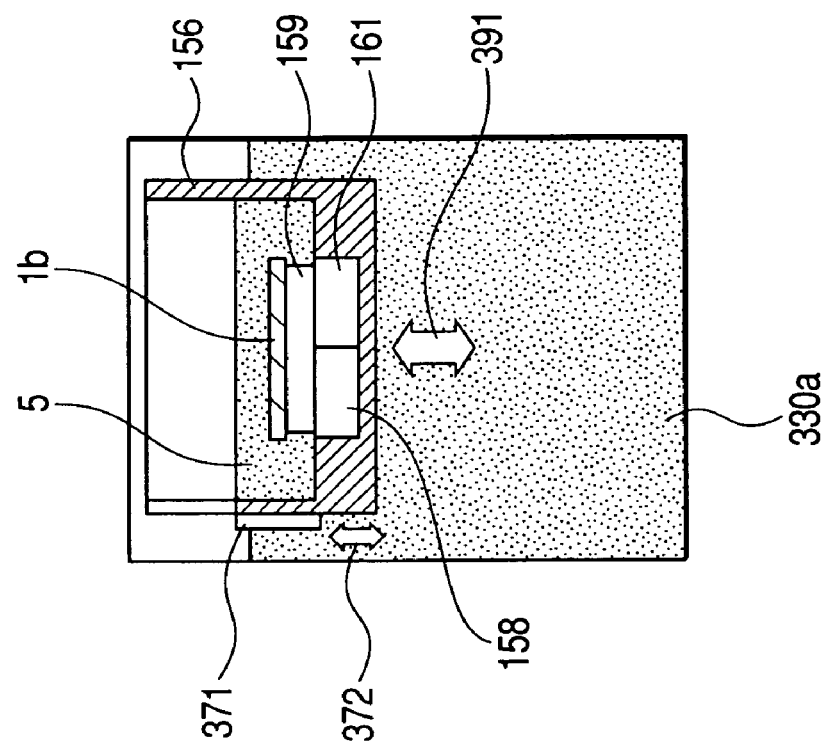

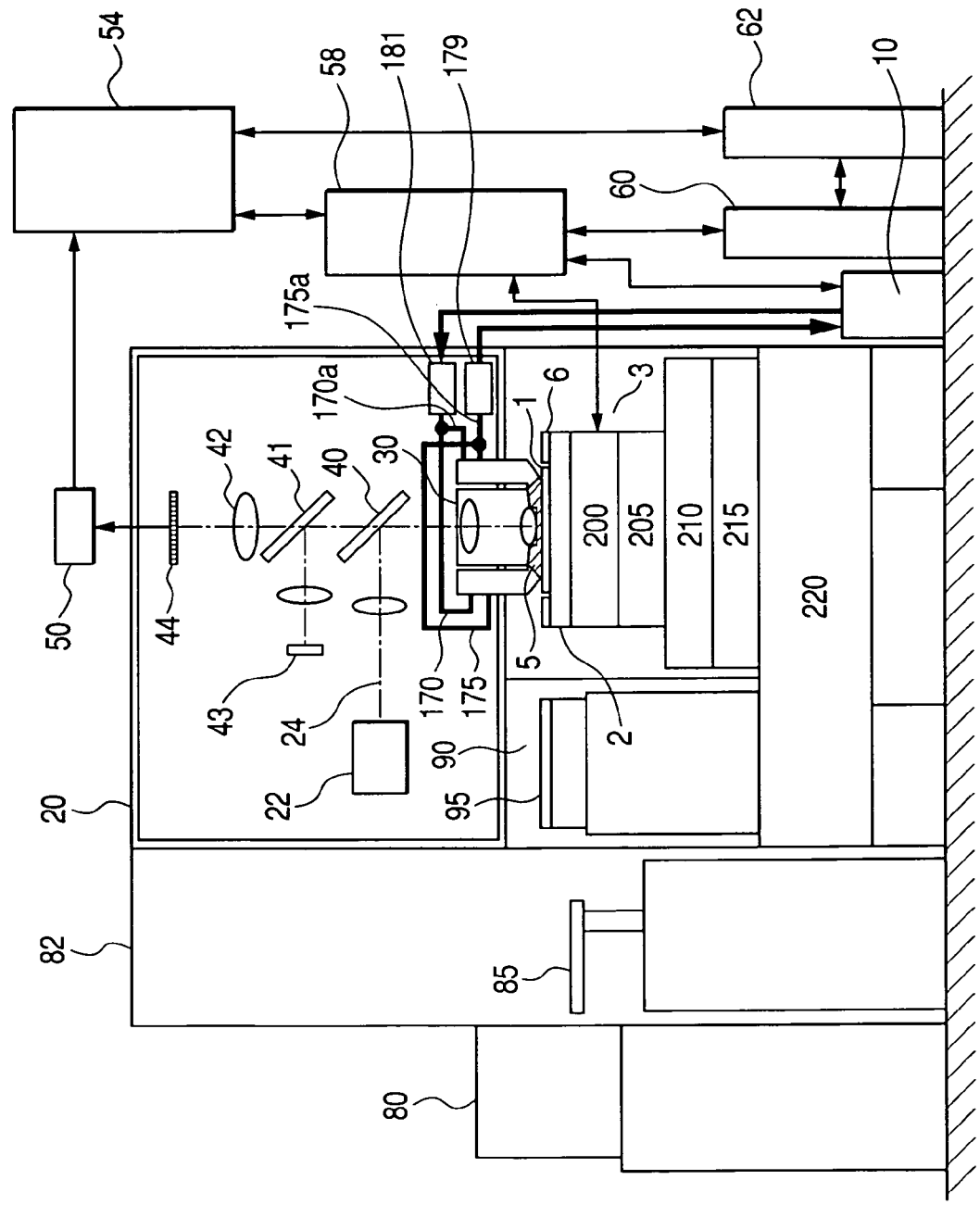

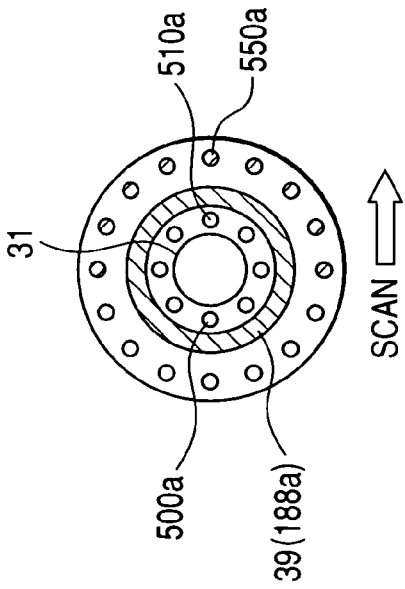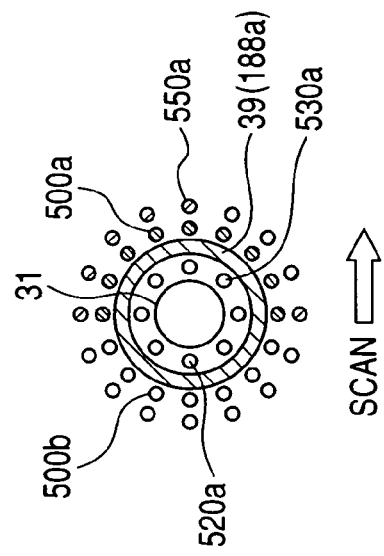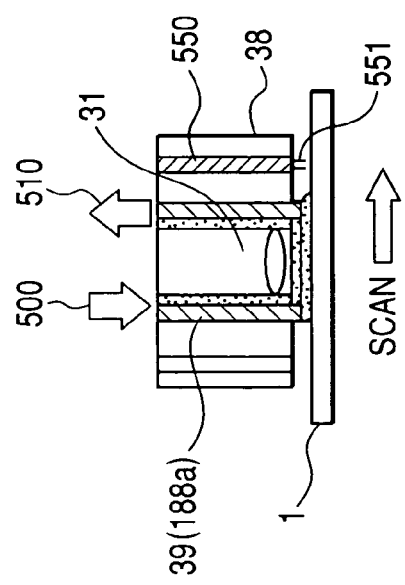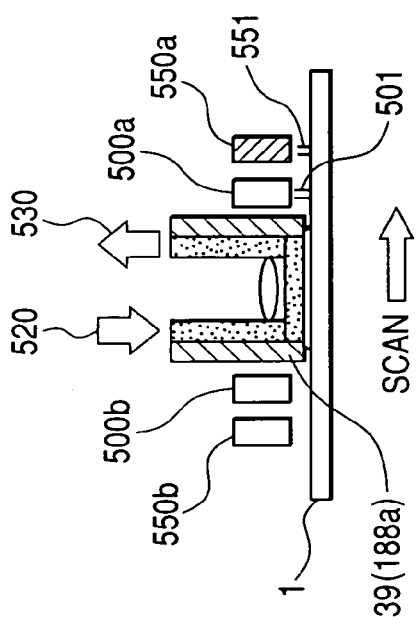

METHOD AND APPARATUS FOR INSPECTING DEFECTS AND A SYSTEM FOR INSPECTING DEFECTS

BACKGROUND OF THE INVENTION

The present invention relates to a defect inspection method, defect inspection apparatus, and defect inspection system used to inspect and observe defects, foreign particles, and the like, on the micropatterns formed on substrates through a thin-film forming process represented by manufacturing processes for semiconductors and/or flat-panel displays.

Fine-structuring of the patterns formed with photolithography is progressing with the enhancement of semiconductor integration density and the improvement of flat-panel display resolution. During the manufacturing processes for these products, the formation of the patterns is followed by defect inspection and/or the like in order to improve production yields. During the defect inspection, the patterns are detected as images by an optical system and then defects are extracted by comparing these images with those of adjacent dies (or cells). When it comes to the generation of sub-100 nm in terms of pattern size, however, optical systems lack resolution and pattern images become difficult to accurately detect. In the field of defect inspection optical systems, therefore, the resolution enhancement technology described in Japanese Patent Laid-Open No. 2000-155099 (corresponding to U.S. application Ser. No. 09/397,334) is known as an ultrahigh-resolution detection technology that uses wavelength reduction, numerical aperture (NA) enhancement, and light polarization.

In response to fine-structuring of technical nodes, wavelength reduction and NA enhancement are also progressing in the field of lithography. At present, the exposure apparatus that uses ArF laser light of a 193 nm wavelength is in practical use, and for further reduction in wavelength, F2 laser light with a wavelength of 157 nm is expected as a promising light source. However, the exposure with F2 laser light, presents problems such as increases in apparatus costs because the construction of an optical system becomes complex and decreases in exposure margins due to decreases in the depth of focus during exposure. For this reason, WO Patent Publication No. WO99/49504 describes the exposure technology that achieves the improvement of resolution and the suppression of decreases in exposure margins at the same time by applying the liquid immersion exposure that uses, for example, ArF laser light as exposure light.

In the above ultrahigh-resolution detection technology that uses light polarization, when a sample is irradiated with specific polarized light via a dry-system objective lens by incident illumination, the light thus reflected/diffracted is captured by the same objective lens and an image of the sample is detected using an image sensor. This conventional technology has had the characteristic that an optical image of the sample can be obtained with high contrast by detecting this image using only specific polarized components of the reflected/diffracted light. However, in a sample, represented by a semiconductor wafer, that has undergone a thin-film forming process, a transparent film made of silicon dioxide ($SiO_2$), for example, is formed as an interlayer-insulating film. This insulating film has thickness unevenness in the wafer. During the inspection, such film thickness unevenness should originally not be detected since it has no fatal influence on device characteristics. During observation through a dry-system lens, however, thin-film interference on the transparent film causes the unevenness of the film thickness to appear as the unevenness of brightness on the image detected. For example, during comparative inspection with respect to adjacent dies, if the transparent films on these adjacent dies are uneven in film thickness, differences in the brightness of the respective images detected will occur and an image of the object will be incorrectly detected as a defect image. Increasing an inspection threshold value in an attempt to avoid such incorrect detection will pose the problem that total inspection sensitivity decreases.

Also, etched patterns are usually subjected to defect inspection. During defect inspection, therefore, sufficient consideration must be given to the fact that the pattern materials varying in type and form and in surface roughness (surface irregularities in level) are used in semiconductor processes.

SUMMARY OF THE INVENTION

In order to solve the above problems, the present invention relates to a defect inspection method, defect inspection apparatus, and defect inspection system which enables defects that are ultrafine than patterns of about sub-100-nm or less to be optically inspected and observed by increasing effective NA for improved resolution.

In one aspect, the present invention is a defect inspection method for detecting with an image sensor the optical image of a sample that has been enlarged and projected by an optical system, and thus detecting defects present on the sample; wherein an object of the present invention is to improve the optical system in resolution by filling the interspace between an objective lens and the sample with a liquid, and increasing effective NA (numerical aperture).

In another aspect, the present invention is constructed so that even when a transparent interlayer-insulating film is formed on the surface of a sample, the unevenness of brightness due to thin-film interference can be reduced since immersion of the interspace between an objective lens and the sample, in a liquid of a refractive index (ideally, 1.3 to 1.7) close to that of the interlayer-insulating film, suppresses amplitude splitting at the interface between the liquid and the insulating film.

Also, in order to prevent air bubbles from sticking to very small pattern surface irregularities (or the like) of the sample, the present invention uses an alcohol-containing liquid to fill the interspace between the objective lens and the sample.

In yet another aspect, the present invention is constructed so that particularly for the liquid immersion inspection that uses pure water, the sample is kept free of air from completion of liquid immersion inspection to that of drying in order to prevent water marks from being formed on the sample by the liquid left thereon.

In addition, the present invention has the features that while being immersed in pure water, the sample that has been inspected by an inspection apparatus is transferred to a cleaning apparatus so as not to form a three-layer interface by the sample, the pure water, and air, and that a drying function of the cleaning apparatus is used as drying means.

That is to say, the present invention is a defect inspection system including: a cleaning tank which chemically cleans a sample and rinses the sample; a defect inspection apparatus equipped with an optical system which illuminates the sample and forms an image thereof, an image sensor which detects the image of the sample, an image processor unit which detects defects by using the image detected by the image sensor, and liquid immersion means by which, at least when the image of the sample is detected, the interspace between the sample and an objective lens of the optical system is filled with a liquid; and a drying tank (a drying means) which dries the sample.

The defect inspection system further has liquid-immersion transfer means which transfers the sample until the sample has been returned from the cleaning tank through the liquid immersion means of the detect inspection apparatus to the drying tank so that the sample is transferred in a liquid-immersed state at least between said cleaning tank and said liquid-immersion means.

The present invention also has the feature that the above-mentioned liquid-immersion transfer means is constructed using a conveyor internally filled with a liquid. In addition, the present invention has the feature that the liquid-immersion transfer means is adapted to accommodate the sample in a liquid-filled cartridge and transfer this cartridge.

In a further aspect, the present invention is a defect inspection apparatus including: an optical system which illuminates a sample and forms an image thereof; an image sensor which detects the image of the sample; an image processor unit which detects defects by using the image detected by the image sensor; local liquid immersion means by which, at least when the image of the sample is detected, a liquid is locally supplied and discharged and the interspace between the sample and an objective lens of the optical system is locally immersed in the liquid; and drying means which dries the sample locally immersed in the liquid by the local liquid immersion means.

Furthermore, the present invention has the feature that the above-mentioned liquid immersion means is adapted to have a supply window for supplying isopropyl alcohol (IPA) as the above-mentioned liquid, and a discharge window for discharging IPA, on peripheral portions at a front end of the objective lens.

Besides, the present invention has the features that the local liquid immersion means formed in a further aspect is adapted to have a pure-water supply window for supplying pure water as the above-mentioned liquid, and a pure-water discharge window for discharging the pure water, in a flange on the periphery of the front end of the objective lens, and locally immerse the flange in the pure water, and that the above-mentioned drying means is adapted to have, on a peripheral portion of the flange, an alcohol-containing liquid supply window for evaporating the pure water left on the sample, and externally to the alcohol-containing liquid supply window, a hot-air window for blasting hot air to dry the sample.

Another object of the present invention is to prevent the flow of a liquid onto the reverse side of a sample by providing discharge means by which, when a peripheral section of the sample is inspected, the droplets of the liquid that leak are held between the sample and an objective lens and then leak from an edge of the sample onto a lateral face thereof are discharged by being taken in by a sample chuck.

According to the present invention, immersing in a liquid the interspace between the objective lens and the sample makes it possible to improve resolution in proportion to refractive index "n" of the liquid, and to suppress the unevenness in the brightness of images of adjacent dies or adjacent cells due to thin-film interference. Hence, inspection threshold values can be reduced and both the above-mentioned resolution improvement and unevenness suppression are effective for improving inspection sensitivity.

Furthermore, according to the present invention, it becomes possible to prevent damage to the sample due to the immersing in a liquid.

These and other objects, features, and advantages of the invention will be apparent from the following more particular description of preferred embodiments of the invention, as illustrated in the accompanying drawings.

BRIEF DESCRIPTION OF THE DRAWINGS

FIG. 7A is a sectional view of a liquid immersion cartridge, showing a state in which the wafer in the second example is chucked using a wafer chucker, and FIG. 7B is a sectional view of a liquid immersion cartridge when it is lifted above the liquid level, on the assumption that the cartridge is a pure-water cartridge;

FIG. 8 is a configuration diagram of a local liquid immersion inspection apparatus which is a second embodiment of the present invention;

FIG. 13A is a front view showing a second example of a front end of an objective lens for local liquid immersion, and FIG. 13B is a schematic diagram of the front end when viewed from the wafer side;

FIG. 14A is a front view showing a third example of a front end of an objective lens for local liquid immersion, and FIG. 14B is a schematic diagram of the front end when viewed from the wafer side;

DETAILED DESCRIPTION OF THE PREFERRED EMBODIMENTS

Embodiments of defect inspection of a liquid immersion scheme according to the present invention will be described using the accompanying drawings.

First Embodiment

Figure 1:
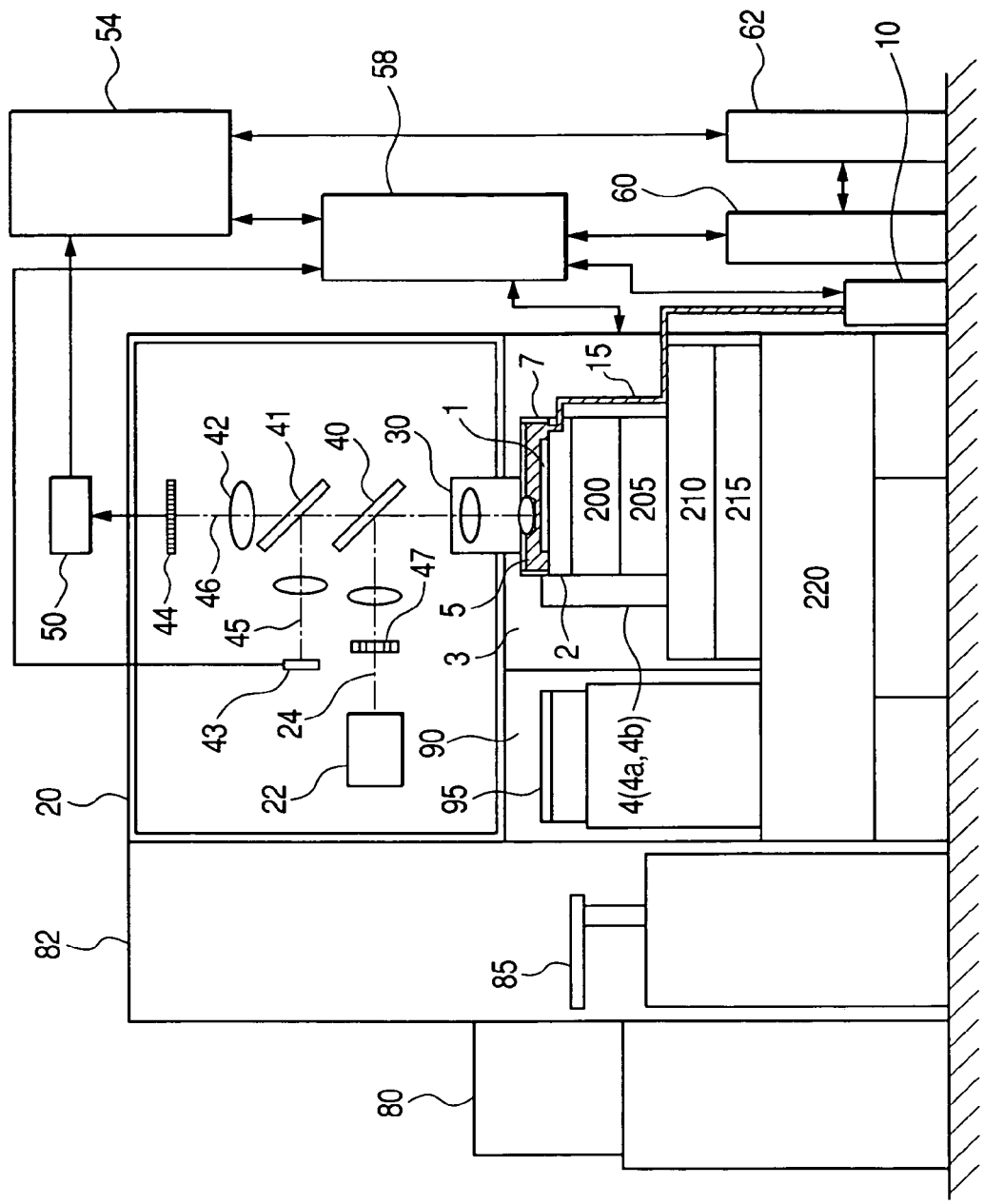
FIG. 1 is a configuration diagram of the inspection apparatus that uses total liquid immersion in a first embodiment of the present invention.

A first embodiment in which the total liquid immersion method that forms part of the liquid immersion technology according to the present invention is applied to an optical-type visual inspection apparatus for semiconductor wafers will be described using FIG. 1. Wafers to be inspected are stored in a cassette 80, and each of the wafers is transferred to an inspection preparation chamber 90 by a wafer transfer robot 85 and then mounted on a wafer notch (or orientation flat) detector unit 95. The wafer is prealigned in a desired direction by the wafer notch detector unit 95. Next, the wafer is transferred to an inspection station 3. In the inspection station 3, wafer 1 is fixed by a chuck 2, and the wafer 1 is totally immersed in a liquid 5 with which a liquid tank (a liquid vessel) 7 is filled. The liquid tank 7 is connected to a liquid supply/discharge unit 10 by a pipe 15, and the liquid tank 7 supplies the liquid 5 after loading of the wafer 1, and discharges the liquid 5 before unloading of the wafer. The chuck 2 and the liquid tank 7 are mounted on a Z-direction stage 200, a θ (rotational)-direction stage 205, an X-direction stage 210, and a Y-direction stage 215. These stages and an optical system 20 which forms an image of the wafer 1 are further mounted on a stone surface plate 220.

Illumination light 24 that has been emitted from a light source 22 of the optical system 20 is reflected by a beam splitter 40 and irradiated onto the wafer 1 via an objective lens 30 and the liquid 5 by means of incident illumination. The light, after being reflected/diffracted from the surface of the wafer 1, passes through the liquid 5 and the objective lens 30 once again and reaches the beam splitter 40. After passing through the beam splitter 40, the light enters a beam splitter 41 that branches a focus detection optical path 45 and an image detection optical path 46. Light that has passed through the beam splitter 41 reaches an image sensor 44 to form an image of the wafer 1 thereon. The image sensor 44 may use the reverse-side irradiation type of charge-coupled device (CCD) array that has high quantum efficiency toward the short-wavelength side. Also, light that has been reflected by the beam splitter 41 is light used to detect an out-of-focus level between the wafer 1 and the objective lens 30, and the light enters a focus detection sensor 43. Focus is detected by, for example, projecting onto the wafer 1 a striped pattern 47 disposed on an illumination optical path, and then detecting with the focus detection sensor 43 an image of the striped pattern 47 reflected by the wafer 1. It is desirable that this image of the striped pattern 47 be spatially separated from the field-of-view detected by the image sensor 44. That is to say, the image of the striped pattern 47 is projected across the field-of-view detected by the image sensor 44 on the wafer 1. A mechanical controller unit 58 calculates contrast of the image thus detected and if defocusing is occurring, the Z-stage 200 is driven for focusing. An optical image formed on the image sensor 44 is thus focused. In the focus detection scheme that uses liquid immersion, high focus-detection accuracy can be obtained by detecting focus with a through-the-lens (TTL) scheme so that the influence of a focus positional change due to unevenness of surface shape of the liquid 5 and temperature of the liquid 5 is not received. Desirably, the light used for focus detection is either light whose wavelength region is equivalent to that of the image formed on the image sensor 44, or light whose chromatic aberration has been corrected for by the objective lens 30.

The image, after being detected by the image sensor 44, is converted into a digital image by an A/D converter 50 and then transferred to an image processor unit 54. In the image processor unit 54, images of adjacent dies (or cells) are compared to extract defects. If the image sensor 44 is of a linear image sensor type such as a TDI (Time Delay Integration) type, images are detected while the wafer 1 is being scanned at a fixed speed. The above-mentioned stages, the wafer transfer robot 85, the liquid supply/discharge unit 10, and the like are controlled by the mechanical controller unit 58. The mechanical controller unit 58 controls the mechanical system in accordance with commands from an operating controller unit 60 which controls the entire apparatus. After defects have been detected by the image processor unit 54, information on the defects is stored into a data server 62. The defect information stored includes defect coordinates, defect sizes, defect classification information, and the like. The defect information can be displayed/searched for using the operating controller unit 60.

While it has been described above that the optical system for illumination uses incident illumination (bright-field illumination scheme), the optical system may use oblique illumination (off-axis illumination: dark-field illumination scheme).

Two advantageous effects obtained from liquid immersion inspection, namely, (1) a resolution improvement effect and (2) a thin-film interference suppression effect, will be described next.

(1) Resolution Improvement Effect

Equation (1) is known as a general equation for calculating resolution R of an optical system.

$$R = \lambda/(2NA) \quad (1)$$

where λ denotes illumination wavelength and NA denotes a numerical aperture of the objective lens.

Also, NA is refractive index "n" between the objective lens and the wafer, and "n" is determined by equation (2).

$$NA = n \cdot \sin\theta \quad (2)$$

where θ denotes an angle range in which the objective lens 30 can capture the lights diffracted/scattered at one point on the wafer 1.

For an ordinary dry-system objective lens, only air is present between the objective lens and a wafer to be inspected, and a refractive index is therefore 1.

Effective NA, however, can be increased by filling an interspace between the objective lens and the wafer, with a liquid whose refractive index "n" is greater than 1.

For example, if the interspace between the objective lens 30 and the wafer 1 is filled with pure water, since a refractive index of pure water is 1.35 (at a wavelength of 365 nm), NA becomes 1.35 times as great as that of the dry-system objective lens. In association with this, resolution also improves by 1.35 times.

An upper limit of NA which can be increased using the liquid-immersion objective lens 30 has a relationship with a total reflection angle of an interface at which the objective lens 30 and the liquid 5 come into contact. If the objective lens 30 uses quartz as a glass material for its front end, refractive index "n1" at a wavelength of 365 nm is 1.48. If pure water is used as the liquid 5, refractive index "n" is 1.35 (at the wavelength of 365 nm). The present embodiment assumes that the surface of the quartz at the front end of the objective lens 30 is parallel to the surface of the wafer 1 facing the lens. When light enters the objective lens 30 from the light source 22, an incident angle of the light totally reflected by the quartz at the front end is defined as a critical angle "θc" determined by refractive index "n1" of the quartz and refractive index "n" of the liquid 5 (here, pure water), as shown in equation (3).

$$\theta c \geq \sin^{-1}(n1/n) \tag{3}$$

The critical angle θc is equivalent to an incident angle of 66°. At this critical angle, no light is allowed to pass through to the liquid 5. For practical purposes, 90% or more of the light passed from the quartz at the front end of the objective lens 30 to the liquid 5 is required (for random polarizing), and the incident angle (angle of incidence from the quartz, on the liquid) in this case becomes about 56°. This angle of 56° is equivalent to an incident angle of 65° on the wafer 1. Accordingly, NA in the liquid 5 is equivalent to 0.91. When converted into an equivalent of a dry-system objective lens, the NA value of 0.91 becomes equal to 1.23. For practical use, therefore, the NA value of 1.23, obtained by the above conversion, is the upper-limit value obtainable at the wavelength of 365 nm. By virtue of the above-described NA enhancement effect obtained using the liquid-immersion objective lens 30, microfine defects unable to be imaged with a dry-system objective lens can be detected as high-contrast images via the liquid-immersion objective lens 30. Hence, defect detection sensitivity can be improved.

(2) Thin-Film Interference Suppression Effect

Figure 2A:
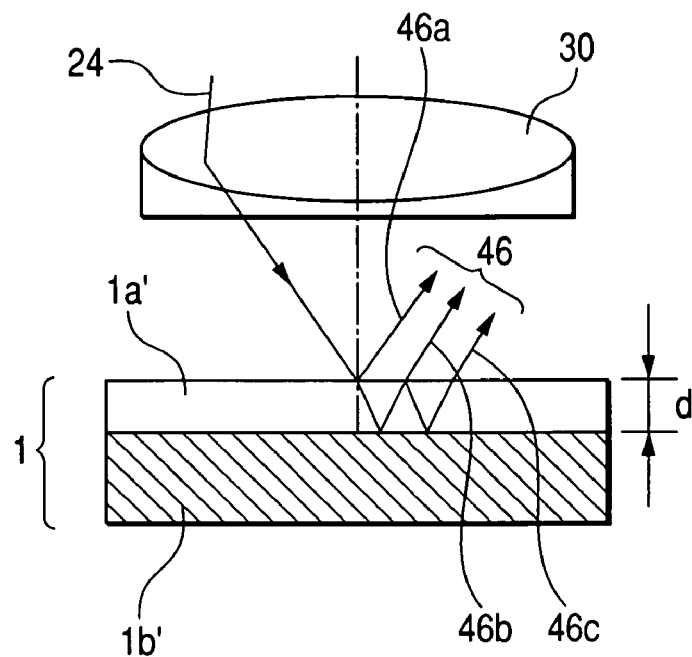
FIG. 2A is a sectional view of a conventional dry-system objective lens and a sample.
Figure 2B:
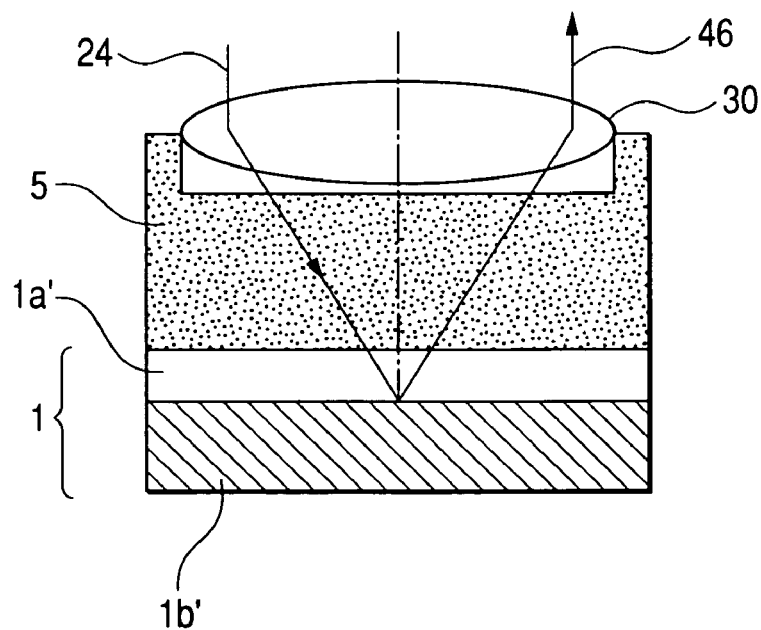
FIG. 2B is a sectional view of an objective lens and a sample, explaining the thin-film interference suppression effect obtained from liquid immersion according to the present invention.

The thin-film interference suppression effect is shown using FIGS. 2A and 2B. A comparative example of thin-film interference suppression using a dry-system objective lens is shown in FIG. 2A. A wafer 1 is illuminated via an objective lens 30. The wafer 1 has a deposited insulating film 1a' (formed of $SiO_2$, for example) on its seed layer silicon 1b'. The insulating film 1a' is optically transparent, and illumination light 24 is amplitude-split into light 46a reflected by a top layer of the insulating film 1a', and light passing through the insulating film 1a'. Light that has passed through the insulating film 1b' is further split into light 46b reflecting from the seed layer 1b' and passing through an interface between air and the insulating film, and light reflecting from the interface. Light that has reflected from the interface between air and the insulating film 1a' repeats multiple reflecting to generate the light, such as light 46c, that comes out into the air. Quality of an optical image formed by the objective lens is determined by interference intensity of the light passed through into the air, such as 46a, 46b, and 46c. The interference is referred to as thin-film interference. Since the intensity of the thin-film interference is a function of a film thickness "d" of the insulating film 1a', if the film thickness "d" becomes uneven, the optical image also becomes uneven in brightness. The unevenness of the film thickness has no fatal influence on device characteristics, and should originally not be detected as a defect. For defect inspection based on die comparisons, however, if the unevenness of the insulating film 1a' in film thickness exists between adjacent dies, since the brightness of the image will also be uneven, the unevenness of the film thickness is more likely to be incorrectly detected as a defect. Although a defect inspection threshold value needs to be increased to prevent such incorrect detection, increasing the threshold value poses the problem that inspection sensitivity decreases.

For this reason, a method for suppressing thin-film interference for improved inspection sensitivity has been desired. This method is shown in FIG. 2B. This method is the same as the liquid immersion method described in above item (1), in which the interspace between the objective lens 30 and the wafer 1 is immersed in the liquid having a refractive index close to that of the insulating film 1a'. In this method, although illumination light 24 illuminates the insulating film 1a' via the liquid 5, if the liquid 5 and the insulating film 1a' have the same refractive index, amplitude splitting at the interface between the liquid 5 and the insulating film 1a' does not occur and all light enters the insulating film 1a'. Light that has passed through the insulating film 1a' reflects from a seed layer 1b' and is captured by the objective lens 30. Accordingly, amplitude splitting does not occur at a top layer of the insulating film 1a', and thin-film interference does not occur, either. Hence, it becomes possible to suppress unevenness of an image in brightness due to unevenness of the insulating film 1a' in film thickness, and thus to suppress incorrect detection of defects due to the unevenness of the film thickness. Consequently, high-sensitivity inspection can be implemented since a trifle small inspection threshold value can be set. If the insulating film 1a' is formed of $SiO_2$, a refractive index thereof is 1.47 at a wavelength of 365 nm. Therefore, the liquid 5 for suppressing thin-film interference due to the unevenness of the insulating film 1a' is preferably a liquid having a refractive index equivalent to that of the insulating film 1a'. However, even when pure water having a refractive index of 1.35 at a wavelength of 365 nm is used as the liquid 5 by way of example, the refractive index of the insulating film 1a' at its top-layer interface does not differ too significantly, compared with the refractive index obtained when a dry-system objective lens is used. A sufficient suppression effect against thin-film interference can thus be obtained. Therefore, the liquid immersion technology using a liquid 5 whose refractive index is greater than that of air (i.e., using a liquid 5 having a refractive index greater than 1) is within the scope of the present invention.

While defect inspection effects based on liquid immersion have been described above, the following three factors need to be considered when a liquid 5 is selected:

(a) In terms of resolution improvement, a liquid higher in refractive index is preferable.

(b) In terms of thin-film interference suppression, a liquid having a refractive index equivalent to that of the insulating film 1a' is preferable.

(c) Since the wafer 1 is to be immersed, a liquid less influential on device characteristics is preferable (this does not apply to destructive inspection.).

Pure water, an alcohol-containing liquid (such as isopropyl alcohol), a fluorine-containing liquid, or even an oil-containing liquid or a mixture of these liquids is likely to be usable as the liquid for liquid-immersion inspection.

Also, the illumination light used for the liquid-immersion inspection is effective anywhere in the range from a visible region to a vacuum ultraviolet region (e.g., 700 to 150 nm in wavelength). The usable types of light sources include a mercury lamp, a Xenon lamp, and other discharge tubes, or a laser light source. In addition, the illumination light can have either a single wavelength width or a broadband wavelength (multispectrum included).

Section 4 (4a, 4b) provided on a lateral face of the stage 200, 205 is an ultraviolet (UV) light irradiating unit for modifying surface characteristics of a front end of the objective lens 30 by surface activation, and/or an objective-lens cleaning tank for cleaning the front end of the objective lens 30. The surface characteristics of the objective lens 30 are modified to prevent air bubbles from sticking to the lens surface, and to create a smooth flow of liquid 5. For these purposes, the lens surface and a lens holder at the lens front end are surface-modified beforehand. For example, the front end of the lens is precoated with a titanium-oxide film to provide hydrophilic treatment. Since the hydrophilic treatment varies characteristics with time, ultraviolet (UV) light irradiating unit 4a for irradiating UV light is disposed at a peripheral portion of liquid tank 7. When the wafer 1 is being unloaded from the chuck 2, the front end of the objective lens 30 is irradiated with UV light from the UV light irradiating unit 4a. This produces a photocatalyzing effect, making it possible to maintain a hydrophilic property. Consequently, it becomes possible to prevent air bubbles from sticking to the lens surface, and to suppress entrainment of the bubbles by making the liquid 5 flow smoothly between the wafer 1 and the objective lens 30. In addition, it becomes possible to prevent false detection of defects without a bubble-laden image being formed in the optical image detected by the image sensor 44 after enlarged projection of the optical image by the objective lens 30.

Furthermore, while the wafer 1 is being unloaded, the front end of the objective lens 30 is immersed in an internal liquid of objective-lens cleaning tank 4b, such as a cleaning liquid (this liquid can be an alcohol-containing liquid, pure water, a fluorine-containing liquid, or liquid 5 for liquid immersion). At the same time, the hydrophilic property is also improved by irradiating UV light from the UV light irradiating unit 4a onto the front end of the objective lens 30 through a transparent window provided at the bottom of the objective-lens cleaning tank 4b. As a result, the front end of the objective lens 30 is protected from dirt and the like. Deterioration of optical image quality can also be prevented.

The above is described in U.S. application Ser. No. 10/893,988.

Features of the first embodiment of the present invention will be described next.

Figure 3B:
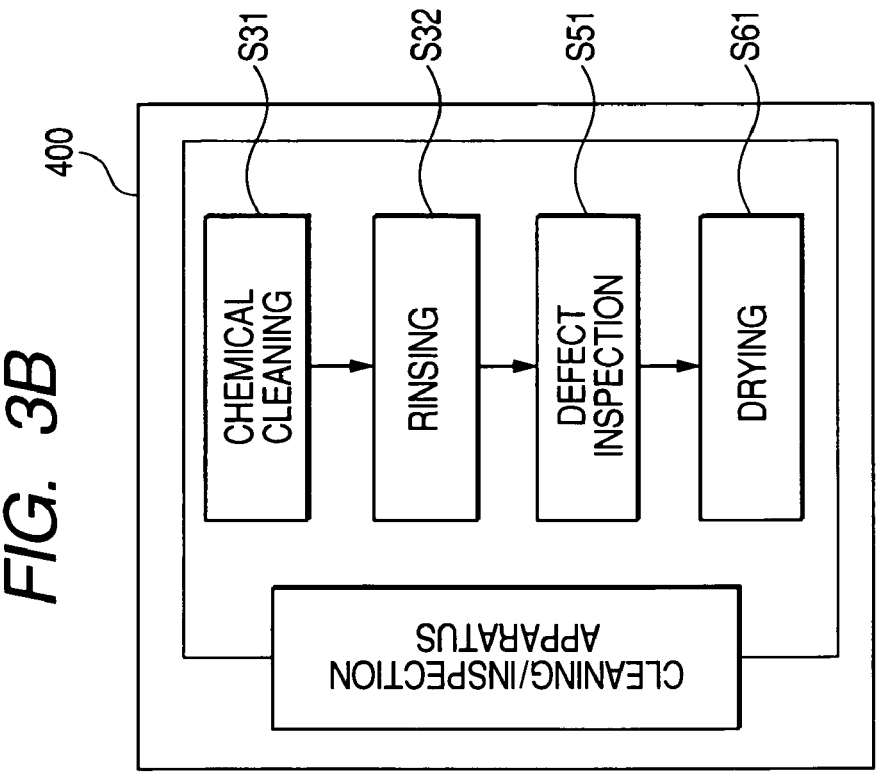
FIG. 3B is a flowchart showing the flow of process steps in a first example of the present invention.
Figure 3A:
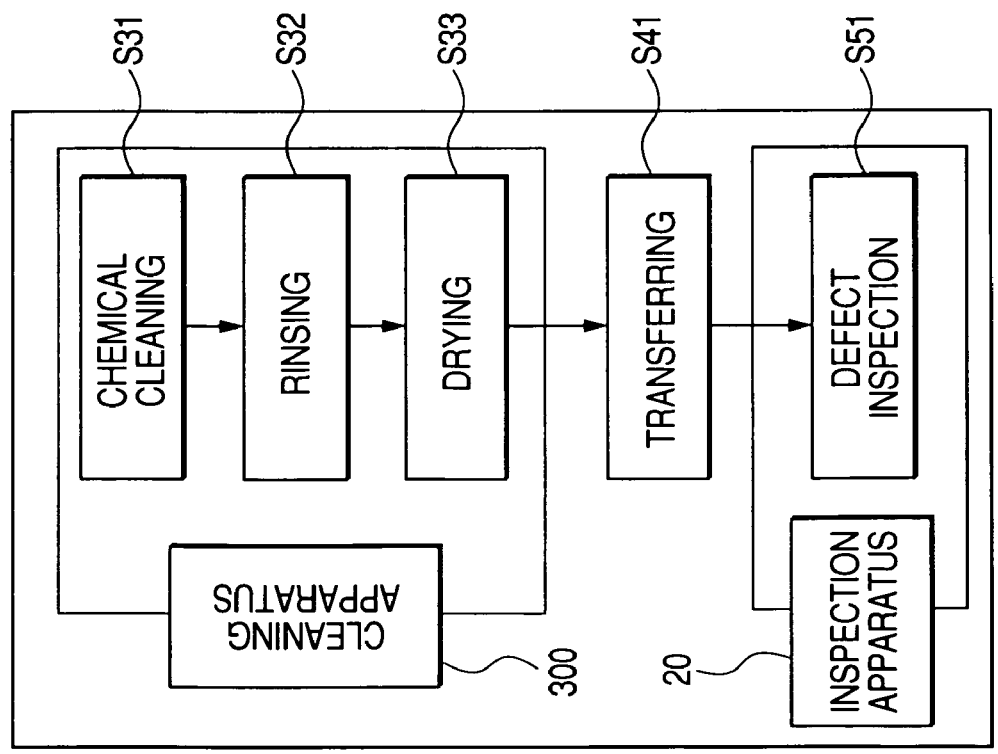
FIG. 3A is a flowchart showing the flow of the process steps, from cleaning to inspection, that use a conventional technology.

Semiconductor wafer pattern processing steps from cleaning to inspection are shown in FIG. 3A. In these processing steps, the pattern formed on a wafer 1 undergoes etching and chemical-mechanical polishing (CMP) and then the wafer is cleaned. In a cleaning apparatus 300, after removal of contamination by chemical cleaning (step S31), the wafer 1 is rinsed in pure water or the like (step S32). After this, the wafer surface is dried using a drying function (step S33). The dried wafer 1 is transferred to an inspection apparatus 20 (step S41). After liquid-immersion inspection by the inspection apparatus 20 (step S51), there is a need to prevent watermarks from occurring. To implement this, the wafer 1 needs to be sufficiently dried when lifted off from a liquid tank 7. When a section to be inspected is a transistor layer of LSI, in particular, insufficient drying is liable to result in watermarks occurring. Therefore, a drying function also needs to be added to the inspection apparatus 20. Adding this function increases an apparatus cost of the inspection apparatus.

Accordingly, a first example 400 of a method for suppressing the apparatus cost in the liquid-immersion inspection which is a feature of the present invention will be described using FIG. 3B. Flow of processing with a system 400 which is the first example is shown in FIG. 3B. The system 400 is a system in which a cleaning/drying function and an inspection function are merged. Chemical cleaning (step S31) of the wafer 1 is followed by rinsing in, for example, pure water (step S32). After rinsing, the wafer 1 is carried in a water-immersed state to inspection station 20 and undergoes liquid-immersion inspection (step S51). After the inspection, the wafer 1 is dried using a drying function of a drying tank (step S61). This makes the liquid-immersion inspection executable without adding a drying function to the inspection apparatus 20. An increase in the apparatus cost of the inspection apparatus, associated with the liquid-immersion inspection, can be suppressed as a result.

Figure 3C:
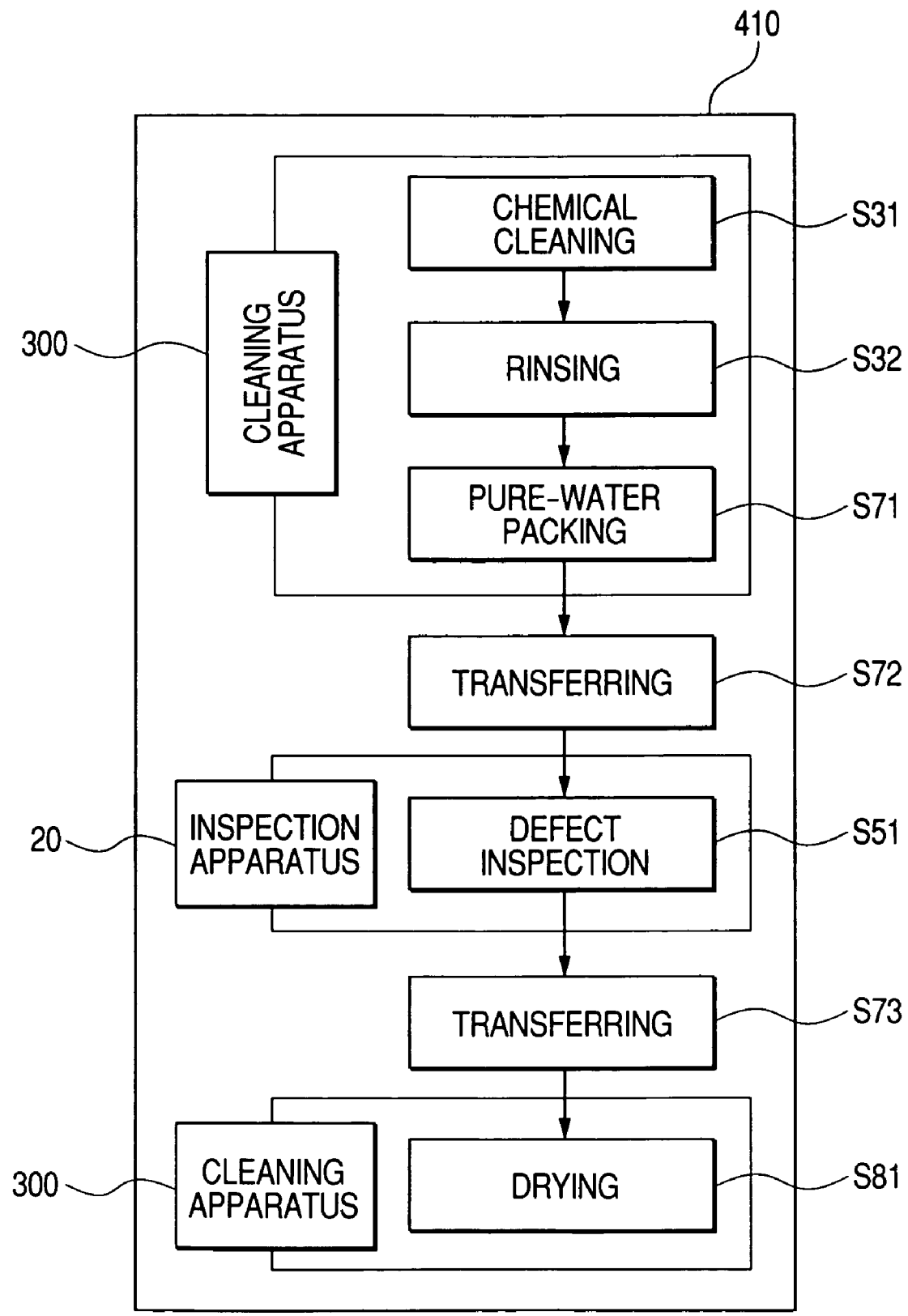
FIG. 3C is a flowchart showing the flow of process steps in a second example of the present invention.

Next, a second example 410 of a method for suppressing the apparatus cost in the liquid-immersion inspection which is a feature of the present invention will be described using FIG. 3C. A system 410 that is the second example is shown in FIG. 3C. The system 410 is a system having a cleaning apparatus 300 and an inspection apparatus 20 linked to each other. The cleaning apparatus 300 is operated to conduct chemical cleaning (step S31) and rinsing (step S32). After rinsing, the wafer 1 is carried in a pure-water immersed state (step S71) to the inspection station 20 (step S72). The pure-water immersed state is called "pure-water packed state" (step S71). The wafer that has been transferred in the pure-water packed state is set up in a liquid tank (a liquid vessel) 7b of an inspection station 20 and undergoes liquid-immersion inspection (step S51). After the inspection, the wafer 1 is once again placed in the pure-water packed state (step S71) and transferred to the cleaning apparatus 300 (step S73). In step S81, the wafer is dried using a drying function of the drying tank 305 mounted on the cleaning apparatus 300. In this linking system 410, wafers 1b and 1c remain in a liquid-immersed atmosphere during process steps from chemical cleaning to inspection. For this reason, the wafers do not come into contact with air up until completion of a drying process by the cleaning apparatus 300 (cleaning tank 330/drying tank 305), based on an isopropyl alcohol (IPA) vapor scheme or the like. This makes it unnecessary to add a drying function to the inspection apparatus 20 and allows watermarks to be prevented from occurring during the liquid-immersion inspection.

Figure 4:
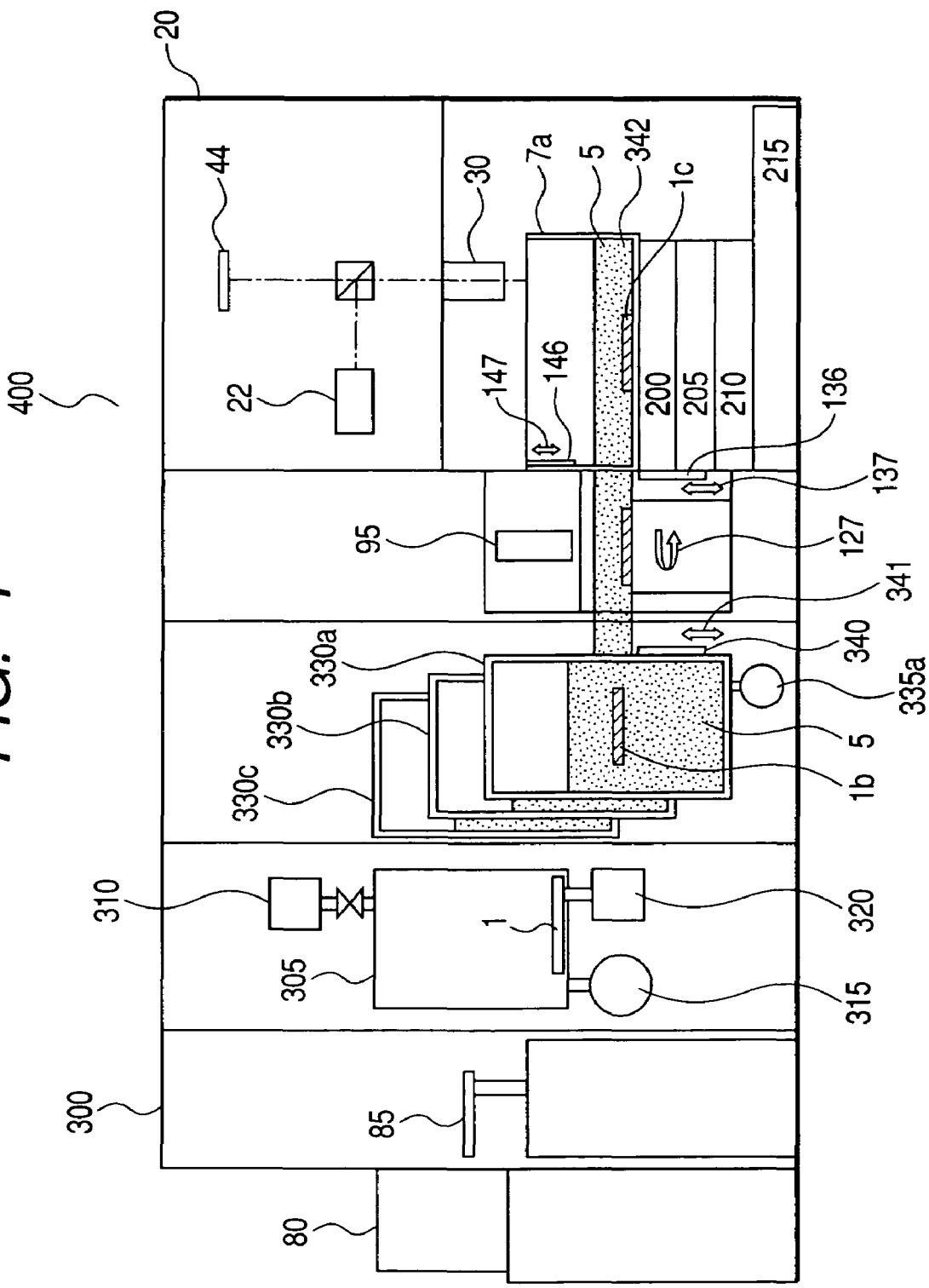
FIG. 4 is a configuration diagram of a cleaning/inspection linking system based on the first example of the first embodiment of the present invention.

Next, an apparatus configuration of the cleaning/inspection process merge system 400 which is the first example will be described in detail using FIG. 4. After wafers store into a cassette 80 following completion of a resist removal process and a CMP process, the each wafer is independently carried from the cassette 80 into a cleaning chamber 330 by a transfer system 85. Depending on the kind of wafer to be cleaned, cleaning chamber 330 has a plurality of liquid tanks (cleaning tanks) 330a, 330b, 330c (water-washing tank included) and conducts cleaning and water-washing processes on a wafer 1b (although a multi-bath configuration is shown in FIG. 4, the above description also applies to a single-bath configuration). A cleaning liquid is supplied from the tank 335a. After final rinsing in pure water, a gate 340 of the liquid tank 330a is opened by an opening/closing unit 341. Through the gate 340, the wafer 1b is carried to a notch detector unit 95 by a liquid-immersion transfer system (liquid-immersion transfer means) 342 (such as the belt conveyor of water that transfers the wafer while keeping it immersed in water 5). The wafer, after being transferred to the notch detector unit 95 by the liquid-immersion transfer system 342, is prealigned in its θ-direction 127. Next, the wafer is carried to an inspection station 20 by the liquid-immersion transfer system 342. At this time, the gate 136 of the notch detector unit 95 and a gate 146 of the inspection station 20 are already opened by respective opening/closing units 137 and 147. The gates 136 and 146 are closed after a wafer 1c has been carried into a liquid tank (a liquid vessel) 7a of the inspection station 20. Since each wafer 1c that has thus been carried into the liquid tank 7a is mounted on an X-stage 215, a Y-stage 210, a θ-stage 205, and a Z-stage 200, the surface of the wafer 1c is visually inspected while an interspace between the objective lens 30 and the wafer remains immersed in pure water 5. After the inspection, the wafer 1c is unloaded through the liquid-immersion transfer system 342. Unloaded wafer 1a is transferred to cleaning/drying chamber 300 (constituted by the drying tank), in which, for example, depressurized/superheated IPA (isopropyl alcohol) vaporizing is then conducted to dry the wafer. A heating plate 320 regulates an internal temperature of a drying chamber (drying tank) 305 to a required value, then vapors of IPA 315 are fed into the chamber 305, and this chamber is depressurized by a vacuum pump 310. This makes it possible to dry the moisture sticking to the wafer pattern, essentially without bringing the wafer into contact with the atmosphere. After the drying process, the wafer is returned to cassette 80.

The usable methods of drying with the drying tank 305 include (1) depressurized IPA (isopropyl alcohol) vaporizing, (2) wafer spinning, (3) gas jet spraying, and others.

Also, the liquid-immersion transfer system 342 may have (provide) a wafer interfacial bubble-removing element for removing the air bubbles sticking to the wafer 1. Wafer-in-liquid ultrasound vibration by an ultrasound vibration source, wafer-in-liquid spinning by a rotating unit, a depressurizing process for reducing an internal pressure of an inspection preparation chamber provided with the notch detector unit 95, or others can be used for the above bubble-removing element. It becomes possible, by providing such a bubble-removing element in the liquid-immersion transfer system 342, to prevent false detection of defects by preventing air bubbles from sticking to the wafer 1 during its actual inspection. Also, when the wafer 1 to be inspected has a formed contact hole on the surface, an interfacial shape of the liquid 5 on a top layer of the contact hole can be made qualitatively even, which allows an even optical image to be detected from the contact hole and false detection of defects to be prevented.

Figure 5:
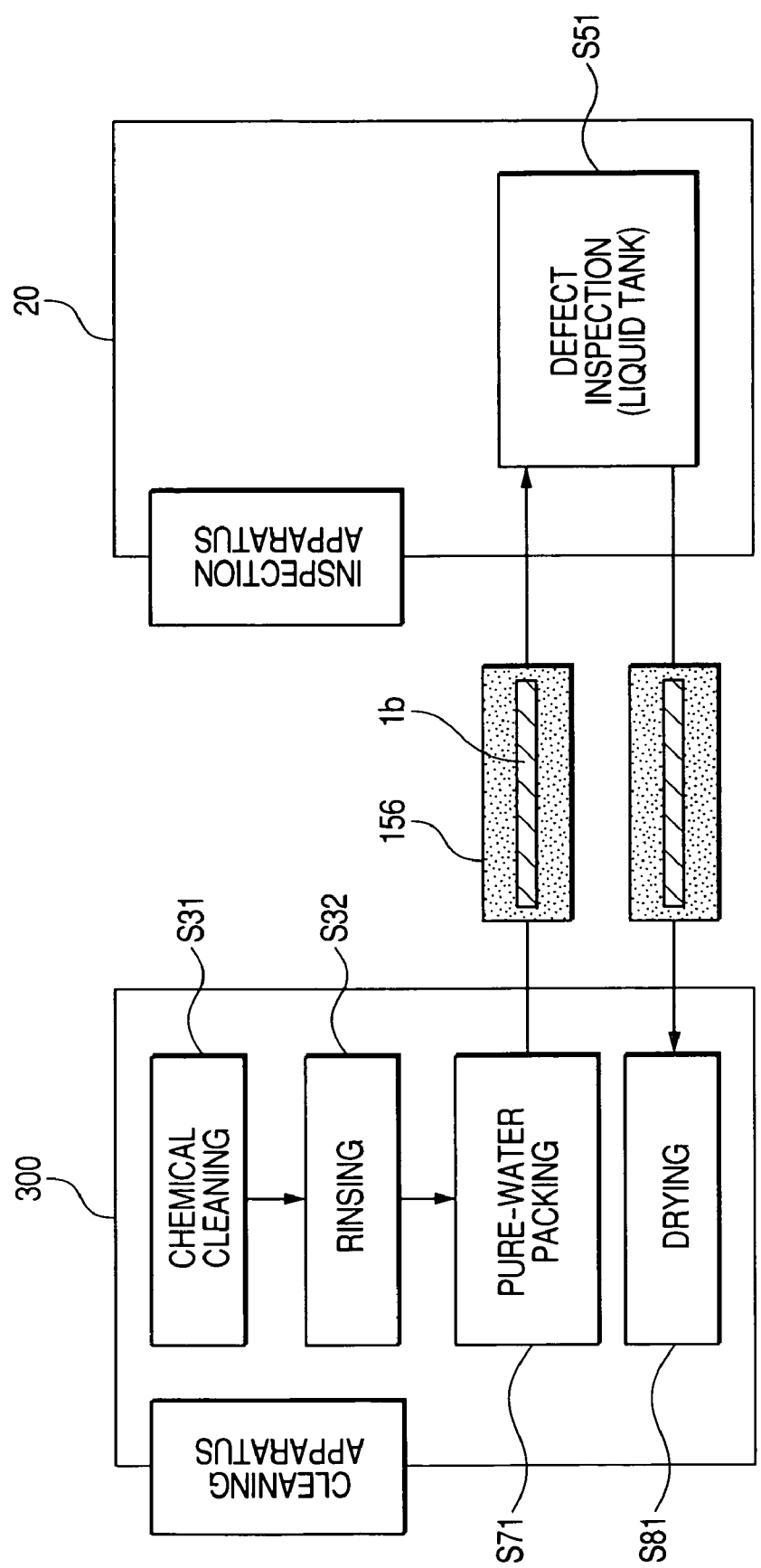
FIG. 5 is a conceptual diagram of the wafer transfer using a liquid immersion cartridge in the first embodiment.
Figure 6:
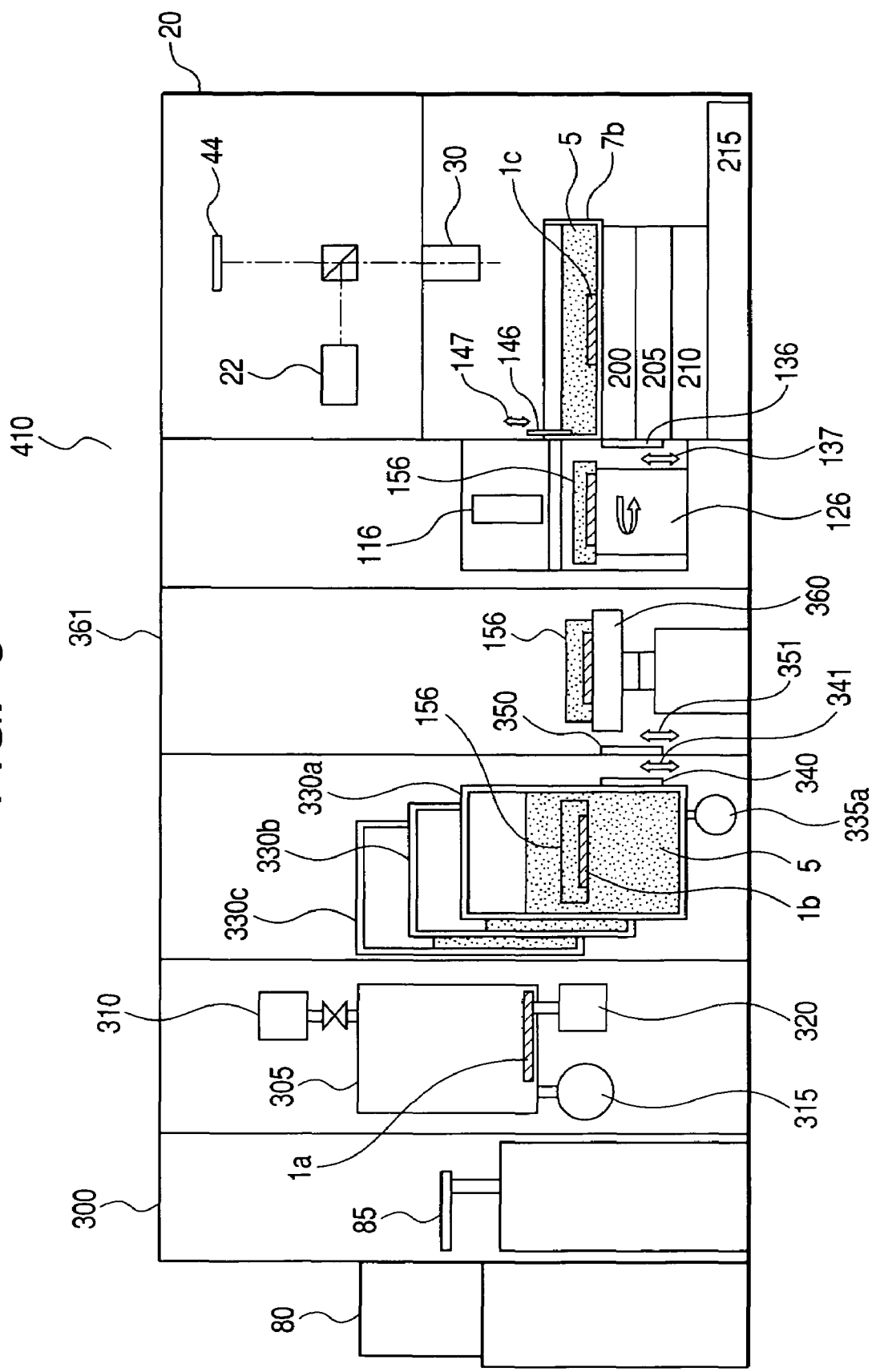
FIG. 6 is a configuration diagram of a cleaning/inspection linking system based on the second example of the first embodiment of the present invention.

Next, an apparatus configuration of the cleaning apparatus/inspection apparatus linking system 410 which is the second example will be described in detail using FIGS. 5, 6, and 7A, 7B. FIG. 5 is a conceptual diagram showing the apparatus configuration of the second example. A wafer 1b is placed in the liquid cartridge (liquid-immersion transfer element) 156 located between the cleaning apparatus 300 and the inspection apparatus 20 and filled with a liquid (e.g., pure water), and the cartridge 156 with the wafer 1b contained therein is transferred. FIG. 6 is a diagram showing a more specific apparatus configuration of the second example. After wafers store into a cassette 80 following completion of a resist removal process and a CMP process, the each wafer is independently carried from the cassette 80 into a cleaning chamber (cleaning tank) 330 by a transfer system 85. Depending on the kind of wafer to be cleaned, the cleaning chamber 330 has a plurality of liquid tanks 330a, 330b and 330c (water-washing tank included) and conducts cleaning and water-washing processes (although a multi-bath configuration is shown in FIG. 6, the above description also applies to a single-bath configuration). A cleaning liquid is supplied from the tank 335a. After final rinsing in pure water, wafer 1b is stored into a pure-water cartridge (pure-water pack) 156. A gate 340 of the cleaning tank and a gate 350 of a transfer system 360 are opened by respective opening/closing units 341 and 351, and thus the pure-water cartridge (liquid-immersion transfer element) 156 is carried to a transfer chamber 361.

The pure-water cartridge 156 is carried to a station of a notch detector unit 116, in which a θ-rotation stage 126 is then rotated to detect a notch in the wafer and prealign this wafer in a θ-direction thereof. The pure-water cartridge 156 containing the thus-prealigned wafer is carried into the inspection station 20, then the wafer 1c remaining immersed in pure water 5 is transferred intact from the pure-water cartridge 156 to a liquid tank (a liquid vessel) 7b, and the wafer 1c is fixed to a chuck of the liquid tank 7b. That is to say, the liquid tank 7b has with a function of chuck 2. In this state, the wafer 1c undergoes liquid-immersion inspection, and after undergoing the inspection, the wafer 1c is returned to the pure-water cartridge 156 and unloaded. During this unloading operation, the pure-water cartridge 156 remains the state filled with the pure water. The system is therefore adapted to keep the wafer not to touch air until it has been dried by a drying function of a drying tank 305. Since the drying tank 305 is internally depressurized by a vacuum pump 310, the wafer is kept almost not to touch air.

Next, a mechanism for storing the wafer 1b into the pure-water cartridge 156 located in the liquid tank 330a of the cleaning chamber, within a rinsing tank, is shown in FIG. 7A. The wafer 1b has a bevel section held by a wafer moving unit 380. After rinsing in pure water 5, a moving arm 381 is slid to chuck the wafer 1b using a chuck 159 of the pure-water cartridge 156. Using an electrostatic chuck or mechanically gripping the bevel section of the wafer 1b is possible as a chucking method. The chuck 159 is driven by the electric power supplied from a battery 158, 161. Next, the wafer moving unit 380 withdraws from the liquid tank 330a and as shown in FIG. 7B, the pure-water cartridge 156 is rotated to place the wafer 1 in a horizontal position. The pure-water cartridge 156 is lifted from the liquid surface by a vertical drive 391. A liquid level of the liquid 5 in the pure-water cartridge 156 is adjusted according to a particular position of a gate 371. After the liquid level in the pure-water cartridge 156 has been adjusted, the gate 371 is closed by a vertical drive 372 in accordance with a wireless signal. In the example of FIG. 7B, the section above, or an upper section of, the pure-water cartridge 156 is not closed. Accordingly, height from the water surface to the top of the pure-water cartridge 156 needs to be controlled considering the occurrence of waves on the water surface due to acceleration during movement.

As described above, according to the first and second examples, since the wafer 1 is kept not to touch air from completion of rinsing by means of the cleaning apparatus 300 to completion of drying, the occurrence of watermarks during liquid-immersion inspection can be prevented without adding a drying function to the inspection apparatus 20. Damage to devices by the occurrence of watermarks can be prevented as a result.

Second Embodiment

A second embodiment in which the local liquid immersion method that forms part of the liquid immersion technology according to the present invention is applied to an optical-type visual inspection apparatus for semiconductor wafers will be described using FIG. 8. Unlike the total liquid immersion method shown in FIG. 1, the local liquid immersion method is used to immerse only the interspace between the objective lens 30 and the wafer 1, in a liquid. A basic configuration of the second embodiment is much the same as that of the first embodiment, except for the inside of the inspection station 3. For example, for a linear type of image sensor 44, images are acquired while the wafer 1 is being moved at a fixed speed. A liquid 5 is fed from a liquid supply/discharge unit 10 into a liquid supply controller 181 at a specific pressure. The liquid, after having its flow rate, temperature, and other factors controlled by the liquid supply controller 181, is supplied to the surface of the wafer 1 through a pipe 170 disposed in front of a position at which the wafer 1 moves past the objective lens 30.

The liquid 5 that has been supplied to the wafer 1 flows under the objective lens 30, in a moving direction of the wafer 1 (here, on the drawing, from left to right). After flowing through the objective lens 30, the liquid 5 is introduced into a liquid discharge controller 179 through a pipe 175a and discharged. The liquid thus discharged into the liquid discharge controller 179 flows out into the liquid supply/discharge unit 10, whereby, even when the wafer 1 is moving, the interspace between the objective lens 30 and the wafer 1 can be filled with the liquid 5 at all times. When the wafer 1 moves in an opposite direction (here, on the drawing, from right to left), the liquid 5 is supplied to the surface of the wafer 1 through a pipe 170a, flows under the objective lens, and is forcibly taken into a pipe 175. When an image is to be acquired during the movement of the wafer 1, therefore, the liquid 5 is supplied in front side of a wafer scanning direction of the objective lens 30 and after flowing through the lens 30, the liquid 5 is discharged. The liquid supply controller 181 and the liquid discharge controller 179 are piped at respective specific water pressures to the liquid supply/discharge unit 10.

Figure 9:
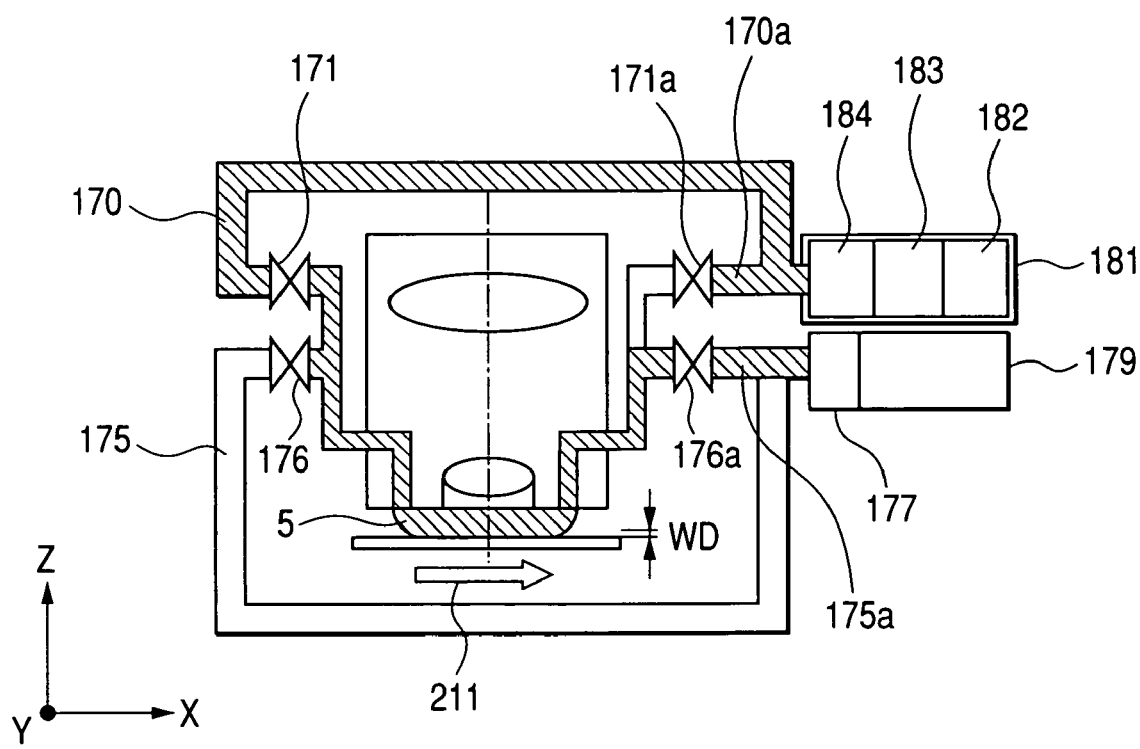
FIG. 9 is an explanatory diagram of the liquid supplying and discharging structure that uses the local liquid immersion method in the second embodiment.

A modification of the local liquid immersion method in the second embodiment is shown in FIG. 9. A flow route of the liquid 5 from the liquid supply controller 181 is branched into two pipes, 170 and 170a. For example, when the wafer 1 is moving at a fixed speed in a direction of arrow 211, a valve 171 on the pipe 170 is open and a valve 171a on the pipe 170a is in a closed state. Hence, the liquid is supplied to the wafer 1 only through the pipe 170. After the liquid 5 has been supplied to the surface of the wafer 1 through the pipe 170, the fluid flows between the objective lens 30 and the wafer 1, and then the fluid is introduced into the liquid discharge controller 179 through the pipe 175a having an open valve 176a. At this time, a valve 176 on the pipe 175 is in a closed state. When the wafer 1 is moving in an opposite direction to that of arrow 211, the valve 171a at the supply side is open and the valve 171 is in a closed state, whereas the valve 176 at the discharge side is open and the valve 176a is in a closed state. Even when the moving direction of the wafer 1 is reversed, the interspace between the objective lens 30 and the wafer 1 can be filled with the liquid at all times by controlling valve opening and closing. The liquid supply controller 181 includes a regulator 182 for regulating a supply rate of the liquid, an in-liquid oxygen concentration regulator 183, and a liquid temperature controller 184. The liquid discharge controller 179 has a mounted regulator 177 for regulating a discharge rate of the liquid.

It is desirable that the oxygen concentration regulator 183 (also having a bubble removal function based on pressure reduction) should be necessary for purposes such as (1) preventing oxidation of the wafer 1 due to the presence of the liquid 5, and (2) removing any microbubbles contained in the liquid supplied. For instance, a device that utilizes Henry's law would be usable as the in-liquid oxygen concentration regulator 183. Also, the liquid 5 changes in refractive index with a change in temperature. Since the objective lens 30 is optically designed with the refractive index of the liquid as a specific value, aberration increases as the refractive index changes more significantly. The temperature controller 184 is therefore required for suppression of changes in the refractive index of the liquid 5. For example, a device that utilizes the Peltier effect (thermoelectric cooling) would be usable as the temperature controller 184. Desirably, even in the wafer total liquid immersion scheme shown in FIG. 1, the oxygen concentration regulator 183 and the temperature controller 184 are provided in the system that supplies the liquid to the liquid tank 7 (7a, 7b), or in the tank 335a.

In particular, when an outer edge portion of the wafer is inspected based on local liquid immersion, since a difference in level for a thickness of the wafer is caused at the outer edge, the liquid flows out from the peripheral edge of the wafer onto the surface of the chuck 2. For this reason, the interspace between the objective lens 30 and the wafer 1 cannot be filled with the liquid. A stepped portion 6 commensurate with the thickness of the wafer 1, therefore, needs to be provided in proximity to an outer portion of the wafer 1 as shown in FIG. 8. Thus, even when the outer portion of the wafer 1 is to be inspected through a pupil of the objective lens 30, the interspace between the objective lens 30 and the wafer 1 can be locally filled with the liquid 5 since a slight clearance is only left between the outer portion of the wafer 1 and the stepped portion 6.

Figure 10:
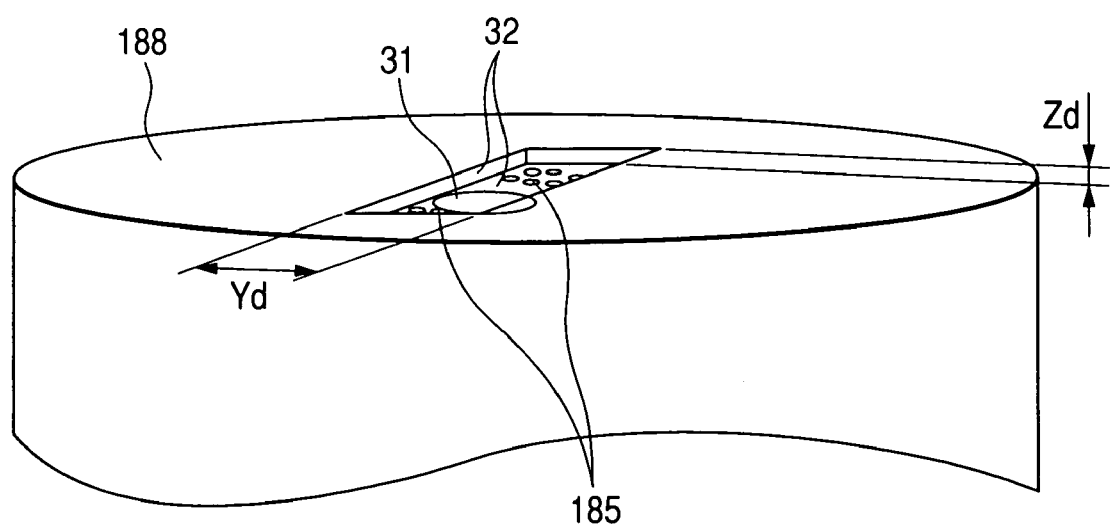
FIG. 10 is a perspective view showing an example of a front-end shape of an objective lens for local liquid immersion.

An external view of the plane of the objective lens 30 that faces the wafer 1 is shown in FIG. 10. Glass 31 is a window that transmits illumination light and the light reflected/diffracted by a pattern. Liquid supply and discharge ports 185 are arranged symmetrically at both sides of the window 31. A groove formed as an interspace having width Yd and depth Zd is a region to be filled with the liquid supplied. Of all faces of the objective lens 30, the plane 188 is brought closest to the wafer 1, and an interspace between the plane 188 and the wafer 1 acts as a working distance (WD). It is desirable that the amount of liquid left on the wafer 1 should be minimized. It is necessary, therefore, for the liquid to be reduced in the amount of overflow reaching a portion other than the groove (e.g., in a direction within a horizontal face, orthogonal to a traveling direction of the wafer 1). A reduction effect against the amount of liquid left on the wafer 1 is expected to be obtainable by conducting hydrophilic surface treatment of grooved portion 32 which is to be filled with the liquid, and hydrophobic (water-repellent) surface treatment of the plane 188 other than the groove. A similar reduction effect is likewise anticipated by adjusting WD. A desirable WD value is up to about 0.7 mm (further desirably, up to about 0.3 mm). A relational expression relating to the amount of liquid supplied and the amount of its discharge, is shown as equation (4) below. When dimension Z for filling the region with the liquid is taken as Zd+WD, dimension Y for filling the region with the liquid as Yd, a stage-scanning velocity as Vst, a liquid supply rate as Vin, and a liquid discharge rate as Vout, liquid supply rate Vin should be greater than liquid discharge rate Vout. This relational expression is shown as equation (4).

$$Vin \geq Vout = (Zd+WD) \times Yd \times Vst \tag{4}$$

As described above, the groove (interspace) 32 to be filled with the liquid is entirely walled by the plane 188.

Figure 11A:
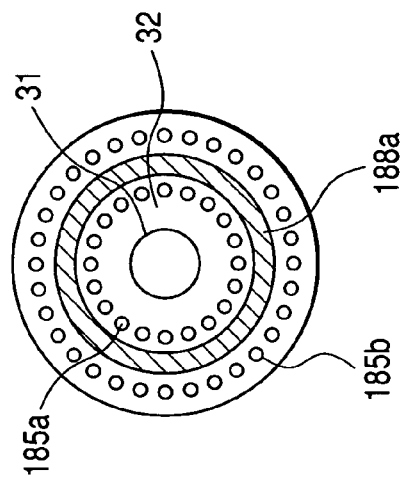
FIG. 11A is a view showing a particular example of a front-end shape of a local liquid immersion objective lens when the front end is observed from the sample side, with the front end being formed with one liquid supply port and one liquid discharge port symmetrically across a window.
Figure 11B:
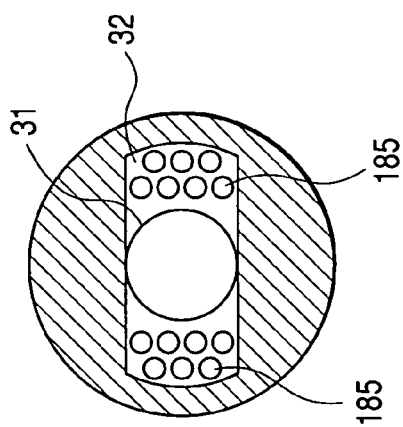
FIG. 11B shows a structure with a plurality of liquid supply ports and liquid discharge ports.
Figure 11C:
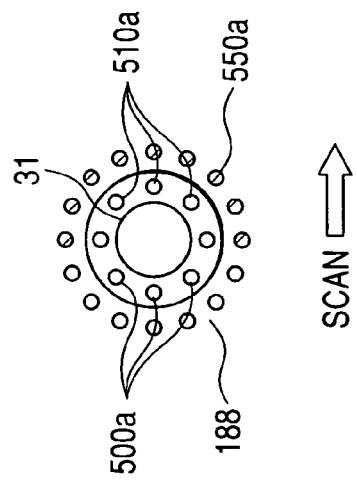
FIG. 11C shows a ring-like formation of the stepped surface closest to the wafer.

As shown in FIGS. 11A, 11B, and 11C, the plane of the objective lens 30 that faces the wafer 1 can take various shapes. At the groove 32 to be filled with the liquid 5, the place 188 is also stepped in a traveling direction of the stage. Examples of shapes of the groove 32 are shown in FIGS. 11A to 11C. In FIG. 11A, two liquid supply and discharge ports 185, one at each side of the window 31, are formed symmetrically thereacross. In FIG. 11B, a plurality of holes are formed as liquid supply and discharge ports 185 at each side. In FIG. 1C, the stepped plane 188 closest to the wafer 1 is formed into a shape of a ring 188a to allow for a two-dimensional movement of the wafer. Internally to this ring, liquid supply ports 185a are formed to supply the liquid 5. Supply of the liquid through an inner-diameter portion of the objective lens results in the liquid overflowing from the stepped plane 188. In order to discharge the overflow, a plurality of discharge ports 185b are arranged externally to the stepped face 188a. The shape thus formed makes it possible, even when the wafer 1 moves in various directions in the plane, to fill an internal section of the stepped face 188a with the liquid and to discharge the liquid. This shape is also effective for purposes such as observing detected defects.

The above is described in U.S. application Ser. No. 10/893,988.

Features of the second embodiment of the present invention will be described next.

An objective lens peripheral construction for local liquid-immersion inspection will be described using FIGS. 12A, 12B, 13A, 13B, and 14A, 14B.

Figure 12A:
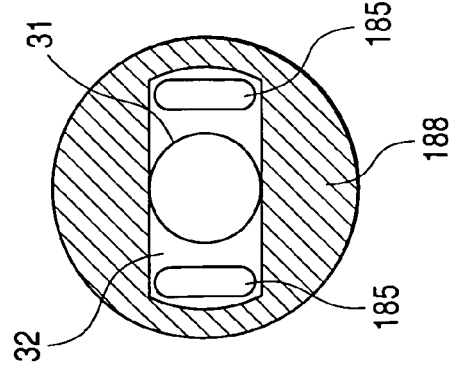
FIG. 12A is a front view showing the mechanism of a front-end lens section in an objective lens group.
Figure 12B:
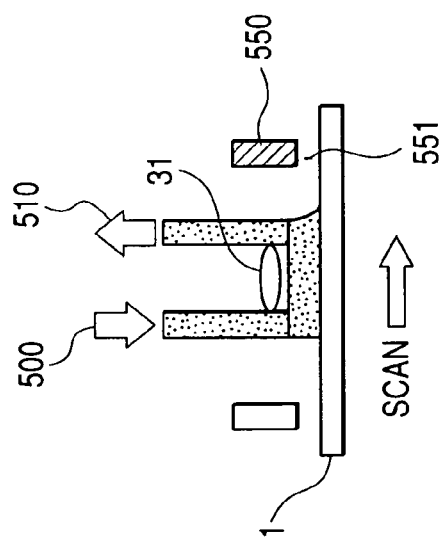
FIG. 12B is a schematic diagram of the front-end lens section when viewed from the wafer side.

First, a first example of the objective lens and periphery will be described using FIGS. 12A, 12B. FIG. 12A is a front view showing a mechanism of a front-end lens portion 31 of the objective lens 30, and FIG. 12B is a schematic diagram of this mechanism when observed from the wafer side. The conceivable kind of liquid would be pure water or isopropyl alcohol (IPA). If pure water is used, watermarks could occur if the water is left on the surface of the wafer 1. When IPA is used as the liquid, however, even if the IPA is left on the wafer 1, the occurrence of watermarks is likely to be suppressible since the IPA evaporates within a short time. In addition, since IPA is most commonly used as a solvent in the drying process that follows cleaning, there is no need to worry about the possible damage to the semiconductor device. Accordingly, the construction that uses IPA as the liquid is shown below.

An IPA supply system 500 supplies IPA to an interspace between the front-end lens portion 31 and the wafer 1. The wafer 1 is scanned in an arrow-marked direction, and IPA is discharged by an IPA discharge system 510. For this reason, there is a liquid immersion effect since the interspace between the front-end lens 31 and the wafer 1 is filled with IPA. However, not all of IPA is completely discharged by the IPA discharge system 510 and part of IPA is left on the wafer 1. Hot air 551 is sprayed onto the wafer 1 by a hot-air blower 550 to evaporate the IPA left on the wafer 1. A schematic diagram of this mechanism when observed from the wafer side is shown in FIG. 12B. The scanning direction of the wafer 1 is from left to right on the drawing. In this case, IPA is supplied from an IPA supply window 500a provided in front side of the wafer scanning direction. The IPA that has passed through the lens is discharged from an IPA discharge window 510a. Furthermore, evaporation of the IPA left on the wafer 1 is accelerated by the hot air 551 blasted through a hot-air window 550a.

When the scanning direction of the wafer 1 is reversed, a function of the IPA supply window 500a and that of the IPA discharge window 510a are changed over to each other and the IPA discharge window 510a and the IPA supply window 500a function as an IPA supply window 500b and an IPA discharge window 510b, respectively. The construction shown in FIG. 9 makes the changeover realizable. A similar changeover also applies to hot-air windows 550a and 550b, and the hot air 551 is blasted from the hot-air window 550b after the wafer 1 has moved past the front-end lens 31. A changeover valve mechanism is also required for the hot air.

Next, second and third examples of the objective lens and periphery will be described using FIGS. 13A, 13B, 14A, and 14B. FIGS. 13A and 13B show the second example in which an area to be filled with IPA is formed into a flange shape. FIG. 13A is a front view of the second example, and FIG. 13B is a schematic diagram of the second example when observed from the wafer side. In a construction of the second example, a wall 39 (188a) is provided on outer surfaces of both an IPA supply window 500 and an IPA discharge window 510.

A construction of the third example in use of pure water as the liquid is shown in FIGS. 14A and 14B. FIG. 14A is a front view of the third example, and FIG. 14B is a schematic diagram of the third example when observed from the wafer side. A pure-water supply window 520 and a pure-water discharge window 530 are provided on an outer surface of the front-end lens 31, and a flange 39 (188a) is internally filled with pure water. That is, when a scanning direction of the wafer 1 is from left to right on the drawing, the flange 39 (188a) is internally filled with pure water by supplying the water from a pure-water supply window 520a and discharging the water from a pure-water discharge window 530a. IPA supply windows 500a and 500b for early evaporation of the pure water left on the wafer 1 are provided externally to the flange 39, and IPA 501 is supplied from these supply windows. Furthermore, hot air 551 is sprayed from a hot-air window 550a onto the wafer previously supplied with IPA. The wafer is thus dried within a short time.

Figure 15:
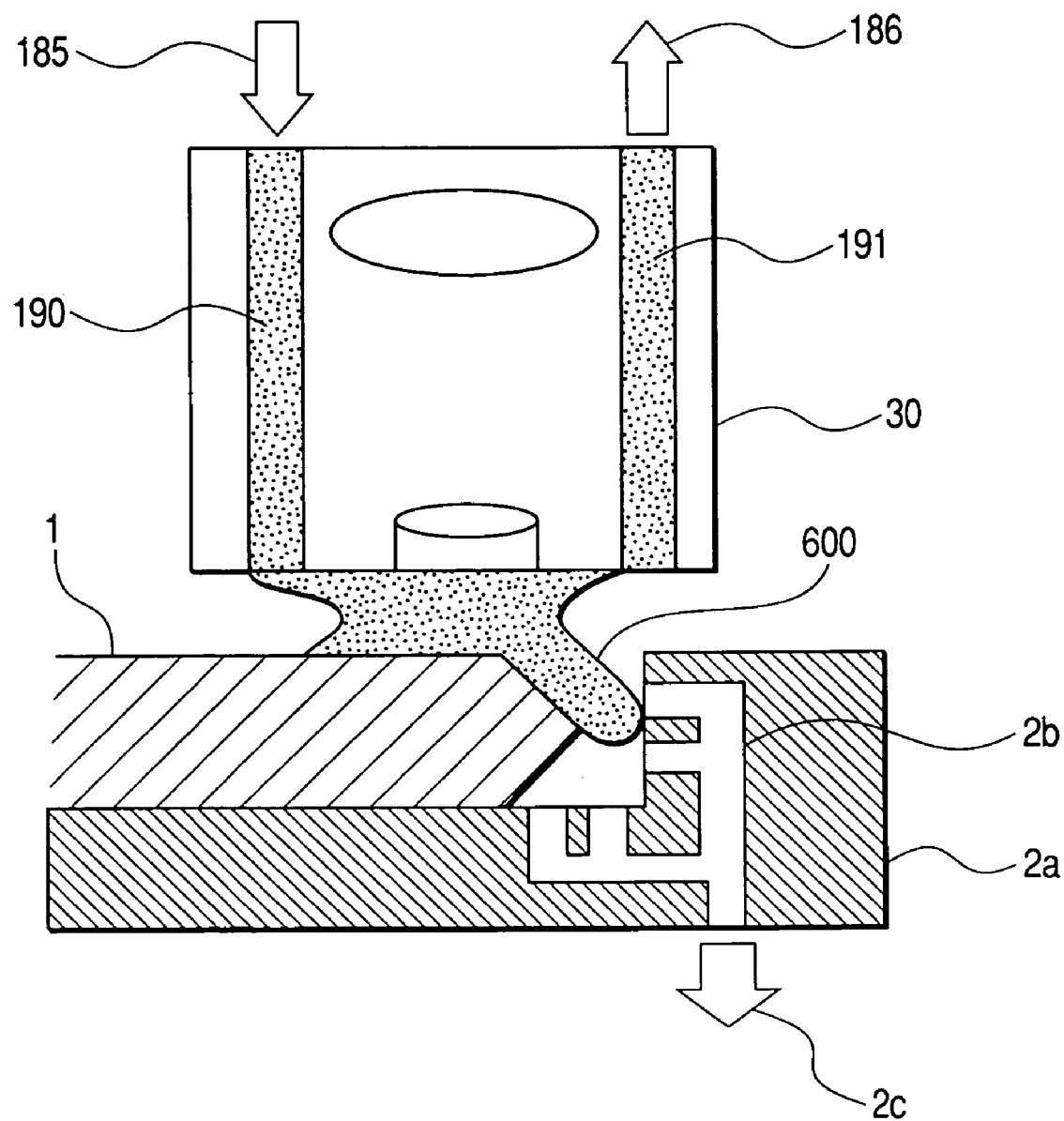
FIG. 15 is a view showing the construction intended to prevent liquid leakage from a wafer edge in the local liquid immersion method according to the present invention.

Next, an example of preventing the liquid from flowing around to the reverse side of the wafer will be described using FIG. 15. During inspection of an outer surface of the wafer 1, the liquid is likely to leak to a bevel section of the wafer when the interspace between the objective lens 30 and the wafer 1 is locally immersed in the liquid by supplying it from a liquid supply system 185 through a liquid supply window 190 to a groove 32 at the front end of the objective lens 30 and discharging the liquid from the groove 32 through a liquid discharge window 191 to a liquid discharge system 186. If the liquid leaks, it will flow around to the reverse side of the wafer and contaminate the bevel section thereof and/or the reverse side of the wafer. However, providing a discharge system 2c by which the liquid 600 that has leaked is taken into a discharge hole 2b of a wafer chuck 2a and discharged makes it possible to prevent the liquid from flowing around to the reverse side of the wafer 1 and contaminating the reverse side thereof.

Third Embodiment

Figure 16:
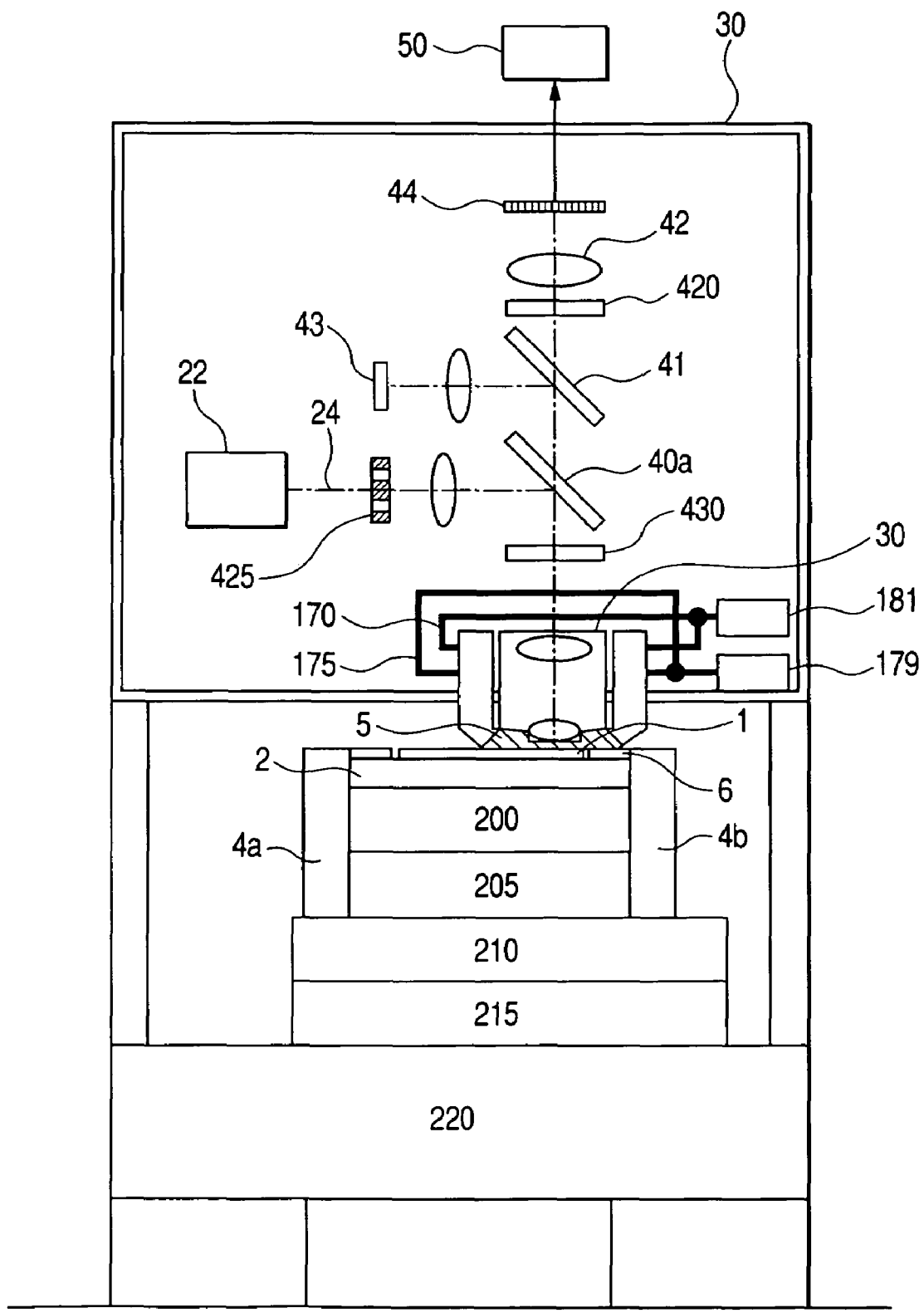
FIG. 16 is a configuration diagram of an optical system in an inspection apparatus which is a third embodiment of the present invention.

Next, an example of configuration of a visual inspection optical system which uses liquid immersion, and a method for improving this optical system in resolution will be described below using FIG. 16.

(1) An interspace between an objective lens 30 and a wafer 1 is immersed in a liquid 5 and thus, resolution is improved.

(2) In an incident illumination/bright-field detection scheme, when Koheler illumination is applied, an image of a light source 22 is formed on an aperture stop (an aperture diaphragm) 425. This image is further formed on a pupil of the objective lens 30. If the aperture stop 425 has a ring-form (zonal) aperture portion, light that illuminates one point on the wafer 1 becomes oblique illumination light not having a vertical illumination light component. Use of the illumination light improves high-frequency MTF (Modulation Transfer Function) of a spatial frequency.

(3) Furthermore, when a polarizing type of beam splitter 40a is used, the light reflected from the beam splitter 40a changes into linearly polarized light. On passing through a wavelength plate 430, the linearly polarized light further changes into elliptically polarized light to conduct the wafer 1 with incident illumination. After the illumination, the polarized light suffers modulation of its polarized state when the light is reflected, diffracted, and/or scattered from a pattern on the wafer 1. These light beams pass through the wavelength plate 430 once again and enter the polarizing-type beam splitter 40a. The P-polarized light that has passed through the polarizing-type beam splitter 40a forms an optical image of the wafer 1, and the image is detected by an image sensor 44. In this way, the polarizing-type beam splitter 40a functions as a light analyzer. Therefore, the polarized state of the illumination light is preadjusted according to the polarized state existing when the light is reflected, diffracted, and/or scattered from the pattern of the wafer 1. Thus, the optical image formed by the regular reflected light, high-order diffracted light, and/or scattered light passing through the polarizing-type beam splitter 40a, is adjusted to become an image advantageous for defect detection. The image advantageous for defect detection refers to an image whose defective portions can be improved in contrast.

(4) When the wafer 1 is illuminated using the ring-form aperture stop 425 described in above item (2), zeroth-order light (regular reflected light) and high-order diffracted light are separated at the pupil of the objective lens 30. For this reason, the patterns on the wafer 1 can be detected in an edge-enhanced state by disposing, at a position of the pupil, a spatial filter 420 for adjusting transmittivity and a relative phase difference for both the zeroth-order light and the high-order diffracted light (first-order or higher). The above is based on the principles of phase contrast microscopy. The pupil of the objective lens 30 is usually formed therein, and therefore, there is no space available to dispose the spatial filter. Hence, a position conjugate to the pupil of the objective lens 30 is provided and the spatial filter 420 is provided at this conjugate position. This makes it possible to enhance optical images in resolution and to form images advantageous for defect detection.

A liquid immersion method is described in above item (1), and a resolution improvement method is described in above items (2) to (4). Combining these methods allows further enhancement of the optical system in resolution and provides a greater advantage in high-sensitivity inspection.

Figure 17:
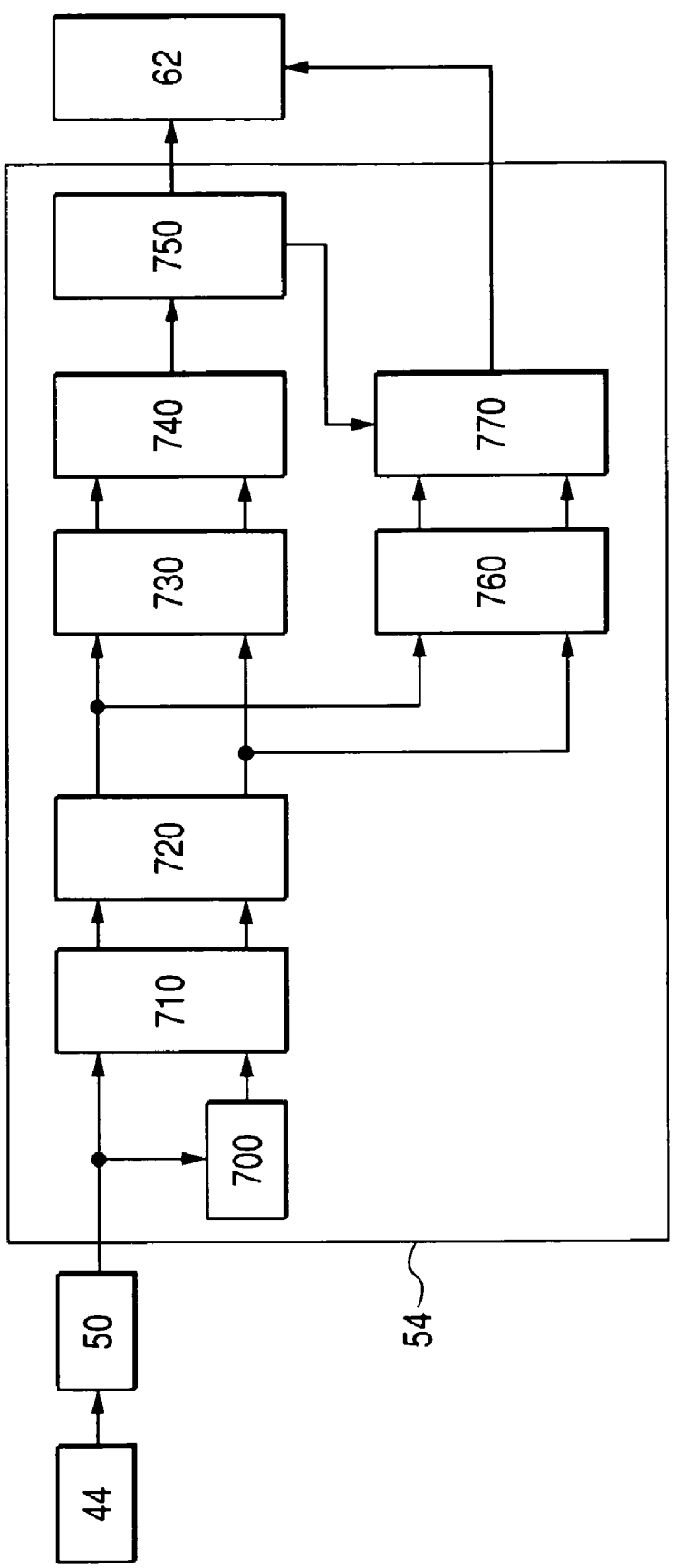
FIG. 17 is a schematic block diagram of an image processor unit in an inspection apparatus according to the present invention.

Next, a more specific example of the image processor unit 54 shown in FIGS. 1 and 8 will be described using FIG. 17. The image of a wafer 1 that has been detected by an image sensor 44 (in the present example, a linear image sensor) is input as a digital image to the image processor unit 54 via an A/D converter 50. The input image is branched into a position deviation detector unit 710 and a delay memory 700. The delay memory 700 sends an image delayed by either a time associated with adjacent dies (in the case of die comparison), or a time associated with adjacent cells (in the case of cell comparison), to the position deviation detector unit 710. The image sent to the position deviation detector unit 710 is therefore an image of an adjacent die (or cell) having the same design pattern formed on the wafer 1. The amount of deviation in position between the above two images is detected by the position deviation detector unit 710 and then the deviation is adjusted for accurate position matching at an image alignment unit 720. Position matching at the image alignment unit 720 is conducted in sub-pixel units.

A differential image between the position-matched images is acquired by a differential-image arithmetic unit 730. Based on characteristic values of the differential image, a judgment is conducted on a defect candidate 750 by a defect-judging unit 740. The characteristic values serving as the base for defect judgment by the defect-judging unit 740 include a gray scale difference, a size (including a area and a projection length) exceeding a gray scale difference threshold, brightness of the detected image, contrast of the image, and defect coordinate information. After being detected by the defect-judging unit 740, the defect candidate 750 has its defect coordinate information input to a defect classification unit 770. The images of the adjacent dies that were branched from the image alignment unit 720 are temporarily prestored in an image memory 760, and images associated with the coordinates of the defect candidate that have been input to the defect classification unit 770 can be read out from the image memory 760. The defect classification unit 770 classifies defects or defect candidate by using the images of the adjacent dies that have been read out. The information of the classification results and the defect candidate 750 are stored into a data server 62. The presence/absence of foreign particles and pattern defects, fatal influence on device characteristics due to the defect, and the like are judged at the defect sorter 770. The coordinate information and size of and classification results on the defect candidate 750, therefore, are stored into the data server 62, from which various defect information is then further sent for a defect observation step.

While defect inspection methods based on liquid immersion, liquid-immersion inspection sequences, and the like have been described above, combinations of respective embodiments/examples, use of composite illumination, modification and omission of an inspection sequence, and the like are easily devisable and details of these combinations and others are embraced in the present invention.

The invention may be embodied in other specific forms without departing from the spirit or essential characteristics thereof. The present embodiment is therefore to be considered in all respects as illustrative and not restrictive, the scope of the invention being indicated by the appended claims, rather than by the foregoing description, and all changes that come within the meaning and range of equivalency of the claims are therefore intended to be embraced therein.

What is claimed is:

1. A method of inspecting defects, said method comprising the steps of:

cleaning a sample having a pattern formed thereon;

rinsing the sample that has been cleaned;

inspecting defects in the pattern by optically inspecting via an objective lens the sample that has been rinsed; and drying the sample that has been subjected to the defect inspection;

wherein after said rinsing step, the sample is transferred to said inspecting step in a state that the sample is immersed in a liquid; and wherein, in said inspecting step of, the sample is optically inspected via the objective lens in a state of which an interspace at least between the sample and the objective lens is immersed in the liquid.

2. The method of inspecting defects according to claim 1, wherein, in said step of inspecting defects in the pattern, the sample is optically inspected via the objective lens in said state being a state which a whole of the sample is immersed in the liquid.

3. The method of inspecting defects according to claim 1, wherein, in said step of inspecting defects in the pattern, the sample is optically inspected via the objective lens in said state being a state which the interspace between the sample and the objective lens is locally immersed in the liquid.

4. The method of inspecting defects according to claim 1, wherein a surface of the sample with the pattern formed thereon is covered with an optically transparent film.

5. The method of inspecting defects according to claim 1, wherein, in said step of inspecting defects in the pattern, the sample is optically inspected via the objective lens while the sample is continuously moved in said state being a state which the interspace between the sample and the objective lens is filled with the liquid.

6. The method of inspecting defects according to claim 5, wherein, in said step of inspecting defects in the pattern, the sample is optically inspected via the objective lens while the interspace between the sample and the objective lens remains locally filled with the liquid by supplying the liquid to the interspace and then discharging the supplied liquid.

7. The method of inspecting defects according to claim 5, wherein, in said step of inspecting defects in the pattern, the sample is optically inspected via the objective lens by acquiring an optical image of the sample by use of an image sensor while the sample is continuously moved in said state being a state which the interspace between the sample and the objective lens is filled with the liquid.

8. A defect inspection system, comprising:
a cleaning tank which chemically cleans a sample and rinses the sample;
a defect inspection apparatus that includes an optical system for illuminating the sample and forming an image thereof, an image sensor for detecting the image of the sample, an image processor unit which detects defects by using the image detected by said image sensor, and liquid-immersion means which, at least when the image of the sample is detected, fills an interspace between the sample and an objective lens of said optical system, with a liquid;
a drying tank which dries the sample; and
liquid-immersion transfer means which transfers the sample from said cleaning tank through said liquid-immersion means of said defect inspection apparatus to said drying tank so that the sample is transferred in a liquid-immersed state at least between said cleaning tank and said liquid-immersion means.

9. The defect inspection system according to claim 8, wherein said liquid-immersion transfer means is constructed using a conveyor internally filled with the liquid.

10. The defect inspection system according to claim 8, wherein said liquid-immersion transfer means has a cartridge and stores the sample into the cartridge filled with a liquid.

11. A defect inspection apparatus comprising:
an optical system which illuminates a sample and forms an image thereof;
an image sensor which detects the image of the sample;
an image processor unit which detects defects by using the image detected by said image sensor;
liquid-immersion means which, at least when the image of the sample is detected, locally immerses an interspace between the sample and an objective lens of said optical system, in a liquid, by locally supplying and discharging the liquid; and
drying means which dries the sample that has been locally immersed in the liquid by said local liquid-immersion means;
wherein said local liquid-immersion means has, in a flange of a peripheral portion of said objective lens, a pure-water supply window for supplying pure water as the liquid, and a pure-water discharge window for discharging the pure water so as to locally immerse the interspace between the sample and the objective lens in the pure water; and
wherein said drying means has, on an outer surface of the flange, an alcohol-containing liquid supply window for evaporating the pure water left on the sample, and externally to the alcohol-containing liquid supply window, a hot-air window for blasting hot air to dry the sample.

12. The defect inspection apparatus according to claim 11, wherein a chuck that holds the sample has, on an outer portion of the chuck, a discharge portion for discharging the liquid that has leaked from a peripheral edge portion of the sample.

13. The defect inspection apparatus according to claim 11, wherein said local liquid-immersion means changes liquid supply and discharge sides to each other in terms of function according to a particular scanning direction of the sample.

14. The defect inspection apparatus according to claim 11, wherein said local liquid-immersion means has, on an outer surface of a front-end lens portion of said objective lens, a supply window for supplying an alcohol-containing liquid as the liquid, and a discharge window for discharging the alcohol-containing liquid.

15. The defect inspection apparatus according to claim 11, wherein said drying means has a hot-air window for blasting hot air.

* * * * *